(12) United States Patent
Van Der Koijk et al.

(10) Patent No.: US 10,886,026 B2
(45) Date of Patent: Jan. 5, 2021

(54) ADAPTIVE TREATMENT MANAGEMENT SYSTEM WITH A WORKFLOW MANAGEMENT ENGINE

(71) Applicant: ELEKTA, INC., Atlanta, GA (US)

(72) Inventors: Johannes Ferdinand Van Der Koijk, Eindhoven (NL); Scot Evan Hogan, Oceanside, CA (US); Colin Raymond Winfield, Crawley (GB); Alexis Nicolaas Thomas Jozef Kotte, Bunnik (NL)

(73) Assignee: Elekta, Inc., Atlanta, GA (US)

( * ) Notice: Subject to any disclaimer, the term of this patent is extended or adjusted under 35 U.S.C. 154(b) by 493 days.

(21) Appl. No.: 15/556,676

(22) PCT Filed: Mar. 10, 2016

(86) PCT No.: PCT/US2016/021867
§ 371 (c)(1),
(2) Date: Sep. 8, 2017

(87) PCT Pub. No.: WO2016/145251
PCT Pub. Date: Sep. 15, 2016

(65) Prior Publication Data
US 2018/0052962 A1      Feb. 22, 2018

Related U.S. Application Data

(60) Provisional application No. 62/131,102, filed on Mar. 10, 2015.

(51) Int. Cl.
*G16H 10/60* (2018.01)
*G16H 50/20* (2018.01)
(Continued)

(52) U.S. Cl.
CPC .......... *G16H 50/20* (2018.01); *G06F 19/325* (2013.01); *G06F 19/326* (2013.01);
(Continued)

(58) Field of Classification Search
CPC .............................. G16H 20/40; G16H 10/60
See application file for complete search history.

(56) References Cited

U.S. PATENT DOCUMENTS

| 6,666,820 B1 | 12/2003 | Poole |
| 2006/0056589 A1* | 3/2006 | Engelward ............... A61N 5/00 378/65 |

(Continued)

FOREIGN PATENT DOCUMENTS

| AU | 2016228845 A1 | 9/2017 |
| CN | 101421736 | 4/2009 |

(Continued)

OTHER PUBLICATIONS

"Australian Application Serial No. 2016228845, Subsequent Examiners Report dated Jul. 9, 2019", 3 pgs.

(Continued)

*Primary Examiner* — John A Pauls
(74) *Attorney, Agent, or Firm* — Schwegman Lundberg & Woessner, P.A.; Sanjay Agrawal

(57) ABSTRACT

This disclosure relates generally to treatment management systems, which may include a clinical database for storing therapeutic protocols. The system may also include a treatment engine operatively connected to the clinical database. The treatment engine may obtain diagnostic information and select a first plurality of therapeutic protocols from the clinical database based on the obtained diagnostic information and reference protocol data. The treatment engine may calculate a treatment efficacy probability for each protocol using the reference protocol data. The treatment engine may (Continued)

Exemplary Adaptive Radiotherapy Case Database develop a first treatment plan and evaluate intermediate data indicating an altered patient state due to the first treatment plan. The treatment engine may select, based on reference protocol data and adaptive protocol data, a second treatment plan using a second plurality of therapeutic protocols. The selected second treatment plan is adapted based on the clinical objective, the reference protocol data, and the treatment efficacy information.

23 Claims, 14 Drawing Sheets

(51) Int. Cl.
*G06F 19/00* (2018.01)
*G16H 40/20* (2018.01)
*G16H 15/00* (2018.01)

(52) U.S. Cl.
CPC ......... *G06F 19/3481* (2013.01); *G16H 15/00* (2018.01); *G16H 40/20* (2018.01)

(56) References Cited

U.S. PATENT DOCUMENTS

| | | | |
|---|---|---|---|
| 2006/0173663 | A1 | 8/2006 | Langheier et al. |
| 2009/0125334 | A1 | 5/2009 | Krishnan et al. |
| 2009/0271424 | A1* | 10/2009 | Bayliss ............... G06F 16/2246 |
| 2011/0119212 | A1 | 5/2011 | De Bruin et al. |
| 2012/0232930 | A1 | 9/2012 | Schmidt et al. |
| 2013/0110547 | A1 | 5/2013 | Englund et al. |
| 2013/0132312 | A1 | 5/2013 | Lee et al. |
| 2013/0204067 | A1 | 8/2013 | Nord et al. |
| 2015/0006192 | A1 | 1/2015 | Sudharsan et al. |
| 2016/0045768 | A1* | 2/2016 | Yan ...................... A61N 5/1037 600/1 |
| 2017/0173365 | A1* | 6/2017 | Bzdusek ............... G06F 19/321 |

FOREIGN PATENT DOCUMENTS

| | | |
|---|---|---|
| CN | 101821741 | 9/2010 |
| CN | 102016859 | 4/2011 |
| CN | 104471597 | 3/2015 |
| EP | 2365456 | 9/2011 |
| EP | 3268880 A | 1/2018 |
| JP | 2004094621 A | 3/2004 |
| JP | 2009533782 A | 9/2009 |
| JP | 2010508938 A | 3/2010 |
| JP | 2011520195 A | 7/2011 |
| RU | 2017134319 | 4/2019 |
| WO | WO-03107250 A2 | 12/2003 |
| WO | WO 03107250 A2 | 12/2003 |
| WO | WO-2015023674 A1 | 2/2015 |
| WO | WO 2015023674 A1 | 2/2015 |
| WO | WO-2016145251 A1 | 9/2016 |

OTHER PUBLICATIONS

"Russian Federation Application Serial No. 2017134319, Office Action dated Jul. 9, 2019", w English translation, 36 pgs.
International Search Report prepared by the EPO for International Application No. PCT/US2016/021867, 3 pages.
"International Application Serial No. PCT/US2016/021867, International Preliminary Report on Patentability dated Sep. 21, 2017", 9 pgs.
"International Application Serial No. PCT/US2016/021867, International Search Report dated Jun. 17, 2016", 4 pgs.
"International Application Serial No. PCT/US2016/021867, Written Opinion dated Jun. 17, 2016", 7 pgs.
"Australian Application Serial No. 2016228845, Subsequent Examiners Report dated Apr. 29, 2019", 6 pgs.
"Australian Application Serial No. 2016228845, Response filed Jun. 12, 2019 to Subsequent Examiners Report dated Apr. 29, 2019", 24 pgs.
"European Application Serial No. 16711098.0, Response filed Aug. 13, 2018 to Office Action dated Oct. 24, 2017", 18 pgs.
"Australian Application Serial No. 2016228845, First Examination Report dated Jan. 22, 2019", 6 pgs.
"Australian Application Serial No. 2016228845, Response filed Nov. 21, 2019 to Subsequent Examiners Report dated Oct. 31, 2019", 21 pgs.
"Australian Application Serial No. 2016228845, Subsequent Examiners Report dated Oct. 31, 2019", 4 pgs.
"Australian Application Serial No. 2016228845, Subsequent Examiners Report dated Dec. 19, 2019", 6 pgs.
"European Application Serial No. 16711098.0, Communication Pursuant to Article 94(3) EPC dated Aug. 12, 2019", 5 pgs.
"European Application Serial No. 16711098.0, Response filed Feb. 17, 2020 to Communication Pursuant to Article 94(3) EPC dated Aug. 12, 2019", 35 pgs.
"Japanese Application Serial No. 2017-547954, Notification of Reasons for Refusal dated Dec. 3, 2019", W/ English Translation, 10 pgs.
"Japanese Application Serial No. 2017-547954, Response filed Feb. 27, 2020 to Notification of Reasons for Refusal dated Dec. 3, 2019", w/ English claims, 17 pgs.
"Russian Application Serial No. 2017134319, Office Action dated Oct. 23, 2019", w/ English Translation, 18 pgs.
"Russian Application Serial No. 2017134319, Response filed Jan. 15, 2020 to Office Action dated Oct. 23, 2019", w/ English Claims, 21 pgs.
"Russian Federation Application Serial No. 2017134319, Response filed Sep. 9, 2019 Office Action dated Jul. 9, 2019", w/o English claims, 11 pgs.
"Chinese Application Serial No. 2016800147145, Office Action dated Apr. 15, 2020", w English Translation, 20 pgs.
"Japanese Application Serial No. 2017-547954, Notification of Reasons for Refusal dated Jun. 2, 2020", w English Translation, 8 pgs.
"European Application Serial No. 16711098.0, Communication Pursuant to Article 94(3) EPC dated Jun. 3, 2020", 5 pgs.
"Chinese Application Serial No. 201680014714.5, Response filed Aug. 6, 2020 to Office Action dated Apr. 15, 2020", w English claims, 16 pgs.
"Japanese Application Serial No. 2017-547954, Response filed Aug. 7, 2020 to Notification of Reasons for Refusal dated Jun. 2, 2020", w English, Response to Japanese Office Action, 33 pgs.

\* cited by examiner

FIG. 1: Prior Art

FIG. 2: Exemplary Adaptive Radiotherapy Management System

FIG. 3: Exemplary Therapeutic Agent Module

FIG. 4: Exemplary Adaptive Radiotherapy Treatment Management System

FIG. 5: Exemplary Method for Adaptive Radiotherapy Treatment

FIG. 6: Exemplary Adaptive Radiotherapy Case Database

FIG. 7: Exemplary Adaptive Radiotherapy Protocol Database

FIG. 8: Exemplary Adaptive Radiotherapy Task Database

Exemplary Method for Selecting a First Plurality of Clinical Protocols

FIG. 10: Exemplary Method for Evaluating Intermediate Data

Exemplary Method for Selecting a Second Plurality of Clinical Protocols

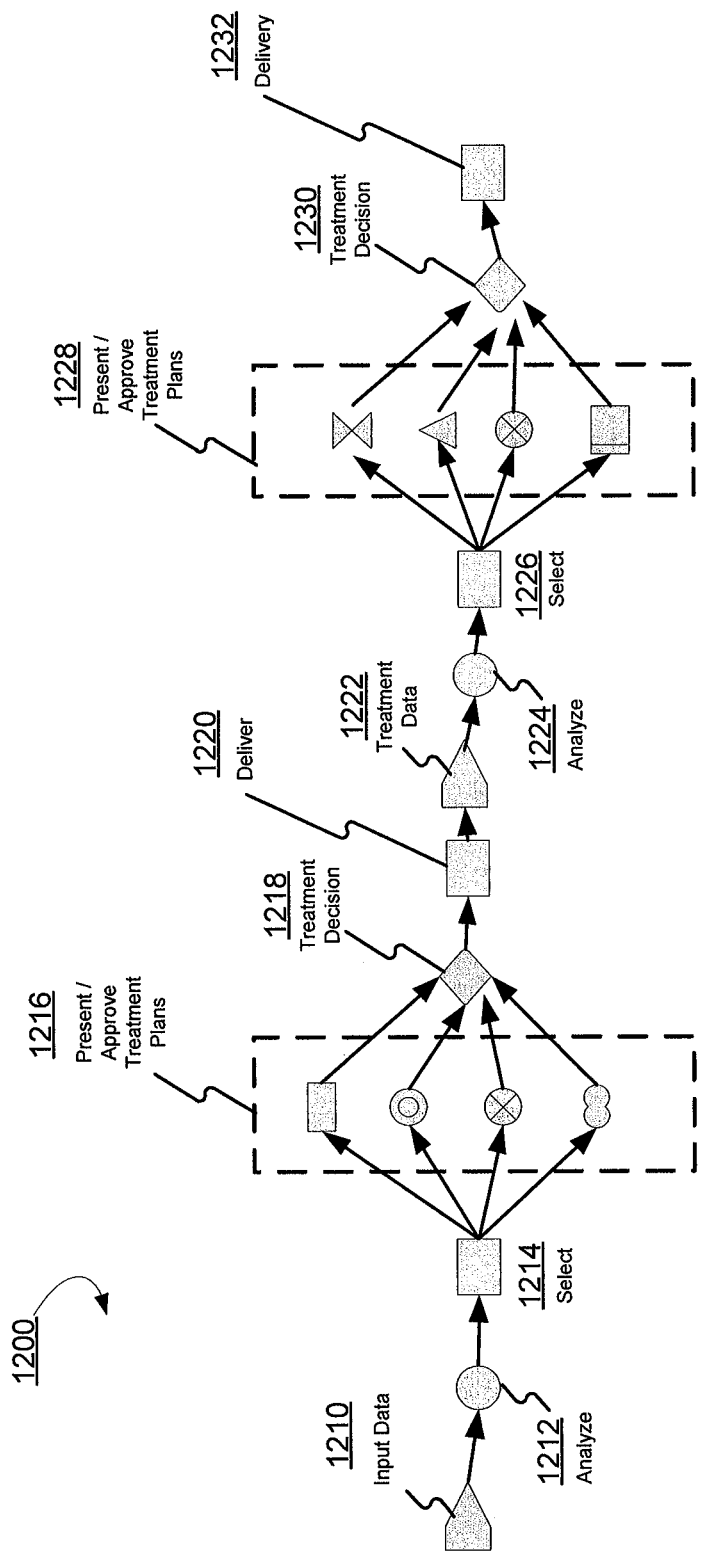
FIG. 12: Exemplary Flow Diagram of Adaptive Radiotherapy Treatment

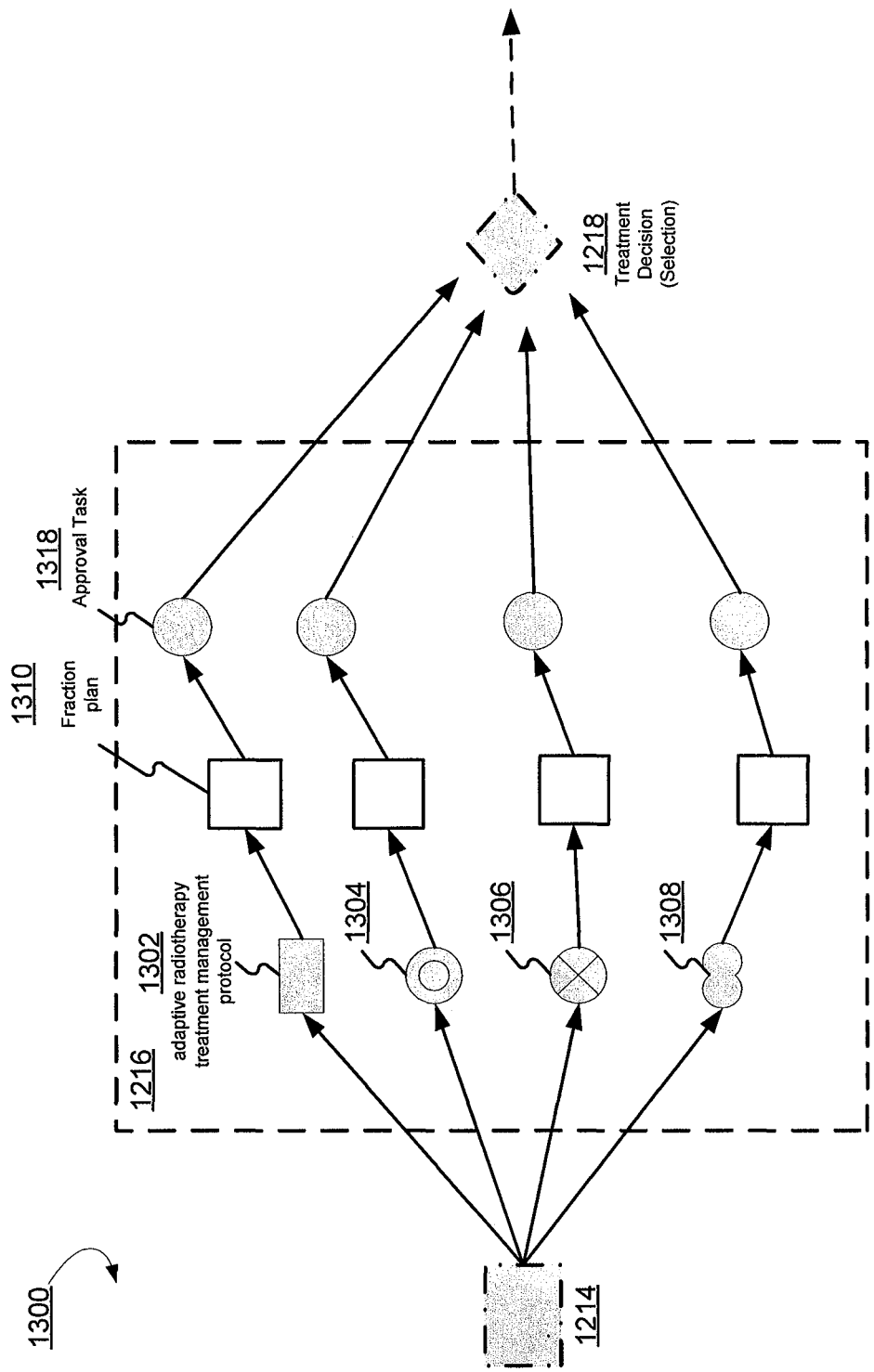
FIG. 13: Exemplary Flow Diagram of Adaptive Treatment Management Treatment Plans

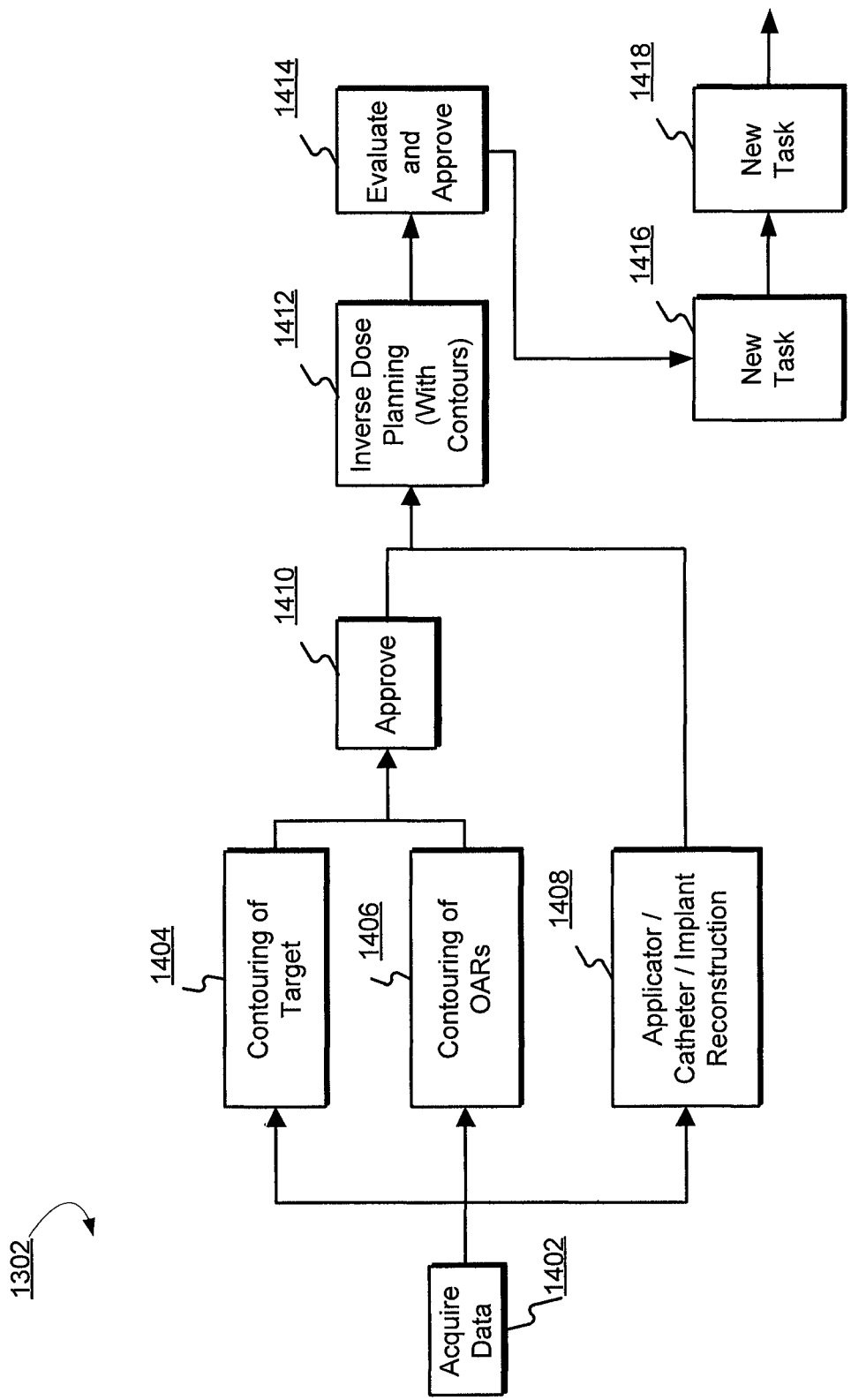
FIG. 14: Exemplary Flow Diagram of an Adaptive Radiotherapy Treatment Management Protocol

ADAPTIVE TREATMENT MANAGEMENT SYSTEM WITH A WORKFLOW MANAGEMENT ENGINE

CROSS REFERENCE TO RELATED APPLICATION

The present application is a US national stage application of International Application No. PCT/US2016/021867, filed Mar. 10, 2016, which claims the benefit of priority to U.S. Provisional Application No. 62/131,102, filed on Mar. 10, 2015, the entire contents of which are incorporated herein by reference.

DESCRIPTION

Technical Field

This disclosure relates generally to cancer treatment management systems, and more particularly to an adaptive treatment management system that provides independent treatment modeling, delivery, and assessment and includes a workflow management engine.

Background

Successful treatment of human cancer requires the elimination of cancer cells while sparing the healthy cells in surrounding tissue. Various therapeutic systems and treatments are used to treat cancer, such as, for example, external beam therapy, brachytherapy, and intraoperative radiotherapy, among others. Radiotherapy cancer treatment may be facilitated by one or more treatment management systems. Radiotherapy treatment management systems can provide workflow planning and support for a variety of therapeutic tasks included in a particular treatment such as, among other things, diagnosis, treatment planning, monitoring, and record keeping. Some systems provide partially automated workflow planning.

In the course of a treatment, medical professionals may have at their disposal various systems and equipment for treating a wide variety of diseased anatomies. Each respective system may provide targeted treatment of particular cancers, such as in the prostate, breast, head and neck, lung, gastrointestinal and reproductive anatomy, among others.

In view of various treatment options for a particular case, an integrated clinical approach may include investigating each of the various approaches to treatment (such as, for example, choosing between electrons, photons, heavy ions, brachytherapy), and comparing each potential treatment option, or a combination thereof, to determine one or more treatment protocols. Various systems may process datasets to create treatment plan candidates from which a plan, or combination of plans, is selected. For example, after investigating many candidate treatment plans, a physician may determine that a combination of plans (e.g., brachytherapy+ external beam radiation therapy) is suitable for the treatment of a particular cancer. As another example, a physician may analyze and compare many different potential protocols of brachytherapy. Accordingly, using an integrated clinical approach, a physician may identify a treatment goal, develop a treatment plan, commit to the plan, execute the plan during a radiation therapy treatment session, and collect and interpret intermediate results with respect to the goal. After considering the intermediate results in view of the goal, the physician may then dynamically adapt the treatment plan based on large volumes of machine-driven data that becomes available over the course of treatment. Such dynamic adaptations may even occur in real-time during a treatment session.

Although it is common practice to retain key information regarding the treatment decision and the clinical treatment itself, persistent records of the intermediate results and predictive analytics of various candidate treatment options considered in light of the intermediate results are currently not maintained. Moreover, to the extent the medical data is quantitatively analyzed by making thousands of comparisons of treatment factors (using, for example, specialized data mining and knowledge management algorithms) while selecting candidate treatment options, the information used to formulate the treatment decision may be stored in one or more independent and disconnected systems and databases. For example, medical images may be stored in a PACS, lab results in the HIS, treatment plans in a TPS, etc. Furthermore, the source data may not be stored in a meaningful format (e.g., machine-readable formats and/or third-party proprietary formats), and the source data may be dispersed among many different systems. Machine-readable formats cannot be interpreted or acted upon by a human, and disparate systems containing pieces of the source data have no integration capabilities. The varying formats and lack of coherent data can diminish the overall effectiveness of future decisions regarding a patient's treatment management. Moreover, the analytical results used in making a treatment decision is not recorded with the treatment decision itself. These factors are magnified when aspects of a treatment plan are performed by various medical professionals at different times in different places.

Many medical devices generate large volumes of digital clinical data used in treatment planning and delivery. These devices include various imaging modalities (CT, MR, PET, SPECT, X-Ray, Ultrasound), segmentation systems, treatment planning systems, hospital and lab information systems, PACS systems and treatment delivery systems. There is currently no system that can provide central management for the various computer-generated medical data, nor is there a system that can provide on-the-spot analysis of the data in order to determine whether a specific treatment should continue or be adapted. Moreover, a need exists for a medical computing system that can automatically record each step in the data analysis process during the specific treatment. The medical computing system can also provide a comparison of treatment options, so that the record of each step during the specific treatment can be accessed and used again for continued or new treatments, or alternatively for retrospective analysis. Moreover, there is no medical computing system that can create a multitude of treatment plans that are based on customized predictions for success, where the predictions are made based on patient specific, case-specific, and multiple patient information. Finally, there exists no medical computing system configured to present these multiple treatment plans to practitioners in an easily-understood format, in real time, without the overbearing presentation of too much data.

Accordingly, there is a need for adaptive cancer treatment management where many different information sources are integrated into a system with flexible treatment planning (e.g., real-time or off-line). Moreover, there is a need for an adaptive system that can learn from information sources as the data is acquired to improve the quality of future treatments suggested by the system.

SUMMARY

This disclosure relates generally to treatment management systems, and more particularly to an adaptive treatment management system for generating treatment plans that provides independent treatment modeling, and that includes a workflow management engine. In one embodiment, a system is described that includes a clinical database for storing therapeutic protocols. Each therapeutic protocol may reflect a plurality of treatment tasks. The system may also include a treatment engine operatively connected to the clinical database. The treatment engine may include a medical device controller configured to obtain diagnostic information, and at least one processor programmed to select a first plurality of therapeutic protocols from the clinical database. The selection may be based on the obtained diagnostic information, and reference protocol data, where the reference protocol data includes updated treatment efficacy information. The treatment engine may calculate a treatment efficacy probability for each protocol in the first plurality of therapeutic protocols using the reference protocol data. The treatment engine may develop a first treatment plan from the first plurality of therapeutic protocols based on a clinical objective, the reference protocol data and the treatment efficacy probabilities, evaluate, during a course of execution of the first treatment plan, intermediate data indicating an altered patient state due to the course of execution of the first treatment plan, and select, based on reference protocol data and adaptive protocol data, a second treatment plan using a second plurality of therapeutic protocols. The selected second treatment plan is adapted based on the clinical objective, the reference protocol data, and the treatment efficacy information.

In another embodiment, a computer-implemented method for generating treatment plans is described. The method may include selecting, using at least one processor, a first plurality of therapeutic protocols from a clinical database. The selection may be based on relevant diagnostic information and reference protocol data. The reference protocol data includes updated treatment efficacy information. The method may further include determining, using the at least one processor, a clinical objective for the treatment plan, calculating, using the at least one processor, a treatment efficacy probability for each protocol in the first plurality of therapeutic protocols using the reference protocol data, developing, using the at least one processor, a first treatment plan from the first plurality of therapeutic protocols based on the clinical objective, the reference protocol data and the treatment efficacy probabilities. The method may further include evaluating, using the at least one processor, during a course of execution of the first treatment plan, intermediate data indicating an altered patient state due to the course of execution of the first treatment plan, and selecting, based on reference protocol data and adaptive protocol data, a second treatment plan using a second plurality of therapeutic protocols. The selected second treatment plan may be adapted based on the clinical objective, the reference protocol data, new diagnostic information, and the treatment efficacy information.

Following the delivery of each treatment fraction, this approach can be applied in the same way using one or more images, dosimetric and biologic uptake data, and/or other diagnostic information collected during the previous treatment fractions. This also applies to a patient starting an additional course of therapy as well.

It is to be understood that the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 12 is a flow diagram illustrating an adaptive radiotherapy treatment, in accordance with some embodiments of the present disclosure.

FIG. 13 is a flow diagram illustrating adaptive radiotherapy treatment plans, in accordance with some embodiments of the present disclosure.

FIG. 14 is a flow diagram illustrating an adaptive radiotherapy treatment management protocol, in accordance with some embodiments of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
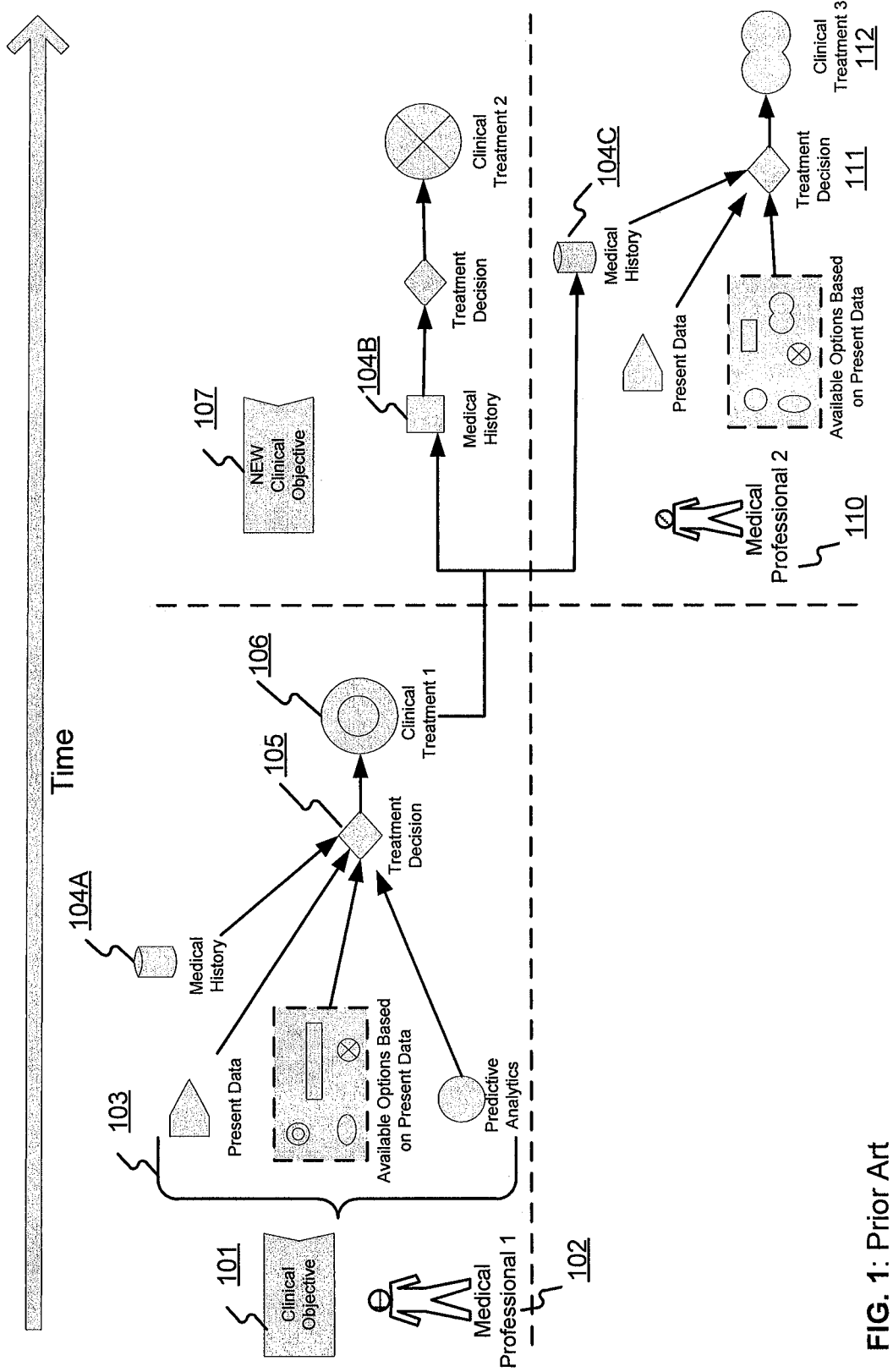
FIG. 1 illustrates the current radiotherapy decision process.

Medical professionals currently use treatment planning and delivery systems that have evolved from a variety of stand-alone systems. Each respective system may deploy linear workflows with a high degree of integration with its environment. For example, in the clinical practice of providing a plurality of treatment fractions in radiotherapy treatment, information learned in a previous treatment fraction may be analyzed to optimize the following treatment fractions. FIG. 1 depicts the current linear workflow (e.g., radiotherapy decision process) in an advanced clinical environment in which a medical professional integrates information learned from a previous treatment into the specific treatment (e.g., current treatment fraction) and application of a new clinical objective determined by workflows, described below.

Referring now to FIG. 1, a medical professional 102 may develop a clinical objective 101 in the treatment of a cancer patient (not shown). The clinical objective, or goal for treatment, may be based on clinical information 103 gathered from workflows which depend on concurrency (e.g., multiple different activities that are temporally and/or sequentially connected to the same snapshot of patient information at a given point in time, for example, a case). For example, clinical information 103 may include data gathered from a currently active treatment session, such as data gathered by one or more image processing devices (e.g., image data showing the contours of organs at risk (OAR) and a target treatment location). During the course of the treatment, the medical professional 102 may analyze intermediate results, and compile the available options based on the present data. Such intermediate results may include, for example, multi-modality images (CT, MR, PET, MV, KV, US), doses delivered to date, lab results, patient vitals, and biological effect metrics. An initial treatment decision 105 is made based on, among other things, the available clinical information 103 and patient medical history 104. The clinical information 103 may also include predictive analytics (e.g., analyses performed by specialized computing systems, for example, utilizing artificial intelligence algorithms) in the analysis of the data and selection of the clinical treatment. After an initial treatment decision 105 is made and the clinical treatment 106 delivered, iterative treatments may be necessary given the patient's predicted and/or observed response. For example, repeating treatment fractions may be clinically required and may be prescribed by the medical professional 102, where information learned in previous treatment fractions (e.g., medical history 104A) is used to optimize future treatment fractions.

In adaptive radiotherapy contexts, medical professional 102 may re-define the clinical objective to create a new clinical objective 107 based on newly available intermediate information. For example, imaging information may indicate that a tumor is not responding to the first clinical treatment 106 (e.g., the tumor fails to shrink based on the amount of radiation prescribed by the treatment fraction). In another example, lab and vital information may indicate the occurrence of undesired side effects of treatment 106 (e.g., organs at risk are responding negatively). One reason for making an adaptive approach to radiotherapy is to improve the probability of tumor control by increasing the therapeutic dose to tumor, while maintaining an acceptable level of short and long term undesired side effects of the treatment to healthy organs and tissues near and surrounding the tumor.

To adapt to a new treatment, the medical professional 102 may open a new path (subcase) in the case having one or more new clinical objectives 107. Although medical history 104B, at this stage of treatment, may now contain the initial treatment decision 105 and the delivered clinical treatment 106, in current practice the various bodies of data and clinical information 103 used to arrive at treatment decision 105 may be saved in a variety of computer-driven medical systems. Because multiple systems may have been previously used to compile clinical information 103, with the passage of time a meaningful persistent record of clinical information 103 used in the formulation of the initial treatment decision 105 may not be maintained (e.g., no overall case view exists, where (sub)systems present their own isolated data). Moreover, the process of determining a specific treatment may have been driven, at least in part, by the personal knowledge and experience of medical professional 102 in view of clinical information 103 for which no meaningful record was created. Without the clinical information 103, the medical professional 102 may not benefit from the record of analysis steps. In other words, no useful link was created between the process of the analyzing the original case and the derivation of new treatment decisions 111 for a new case. Accordingly, clinical treatment 112 may be delivered lacking some previous important information and prior analysis that could have otherwise been provided to the medical professional 110 when making the new treatment decision 111.

This shortcoming of existing radiotherapy workflow management systems arises out of system architectures of previously developed products that were not designed with the flexibility requirements stemming from the plan adaptation capabilities needed for adaptive radiotherapy. Therefore, older architectures used to compile clinical information 103 have led to increasingly complicated radiotherapy workflow system designs which may be inclined to bring with them associated development, deployment and maintenance problems (e.g., forced system rebuild or a change in reliability of existing functionality if a new type of data is introduced). These factors are often magnified when aspects of a treatment plan are performed by a different medical professional 110, at the same time (e.g., making decisions for a current treatment plan), a different time (e.g., making decisions for a future treatment plan), and/or at a different location (e.g., treatment fractions provided at different locations that may occur for the current treatment plan or future treatment fractions). Although the second medical professional 110 may have access to the patient's medical history 104C, new treatment decisions will be made only with the present data and available treatment options, without the benefit of the previous clinical information, reasoning, and analytics used to develop the previous treatment decision. To the extent that this prior information is available, compiling and analyzing the prior information may not be practical based on current radiotherapy workflow systems and products.

The embodiments described herein may provide integrated on-line plan adaptation, concurrency, and flexible data management for radiotherapy clinical workflows. Embodiments apply provenance to persistent recording of clinical data and analyses of data that may be useful for quality assurance compliance to standardized treatment protocols, increasing clinical information useful in future treatments of the same and/or similar patients, and in coordination of workflows at different times and/or locations.

Figure 2:
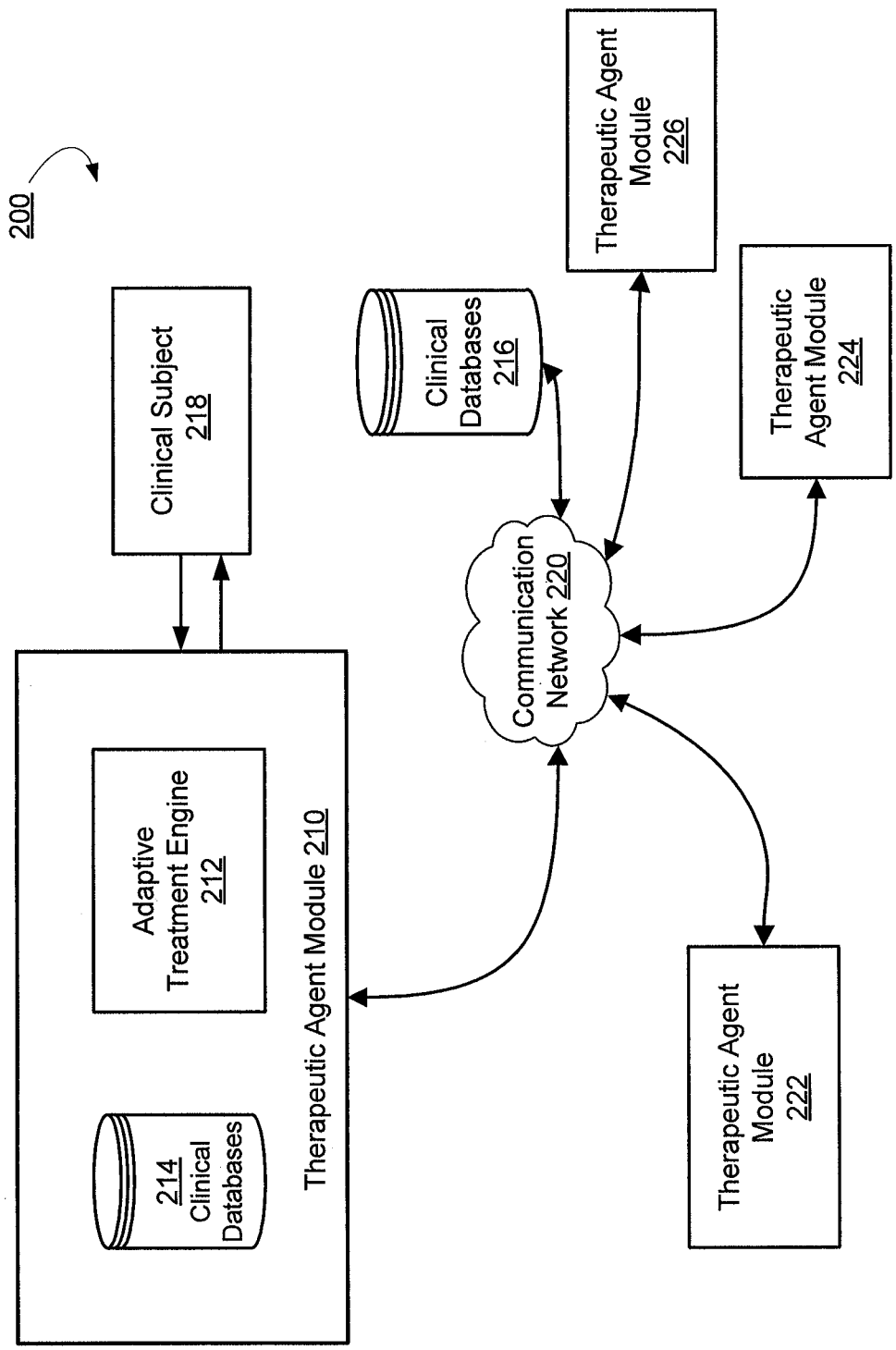
FIG. 2 is a block diagram of an exemplary adaptive radiotherapy management system, according to some embodiments of the present disclosure.

Illustrative embodiments of the present disclosure are described below. Referring now to FIG. 2, an exemplary adaptive radiotherapy management system 200 (hereafter "system 200") is described, according to some embodiments of the present disclosure. System 200 may be configured to provide adaptive radiotherapy treatment to a cancer patient (e.g., clinical subject 218). For example, system 200 may be configured to support and perform diagnosis, treatment planning, treatment delivery, and data management in a radiotherapy clinic.

System 200 may include a therapeutic agent module 210, which may be operatively connected with one or more additional therapeutic agent modules (e.g., 222, 224, and 226) connected via communication network 220. Therapeutic agent module 210 may be operatively connected to a clinical subject 218. Therapeutic agent module 210 may include an adaptive treatment engine 212, and one or more clinical databases 214. System 200 may also include one or more clinical databases 216 in connection with communication network 220.

Figure 3:
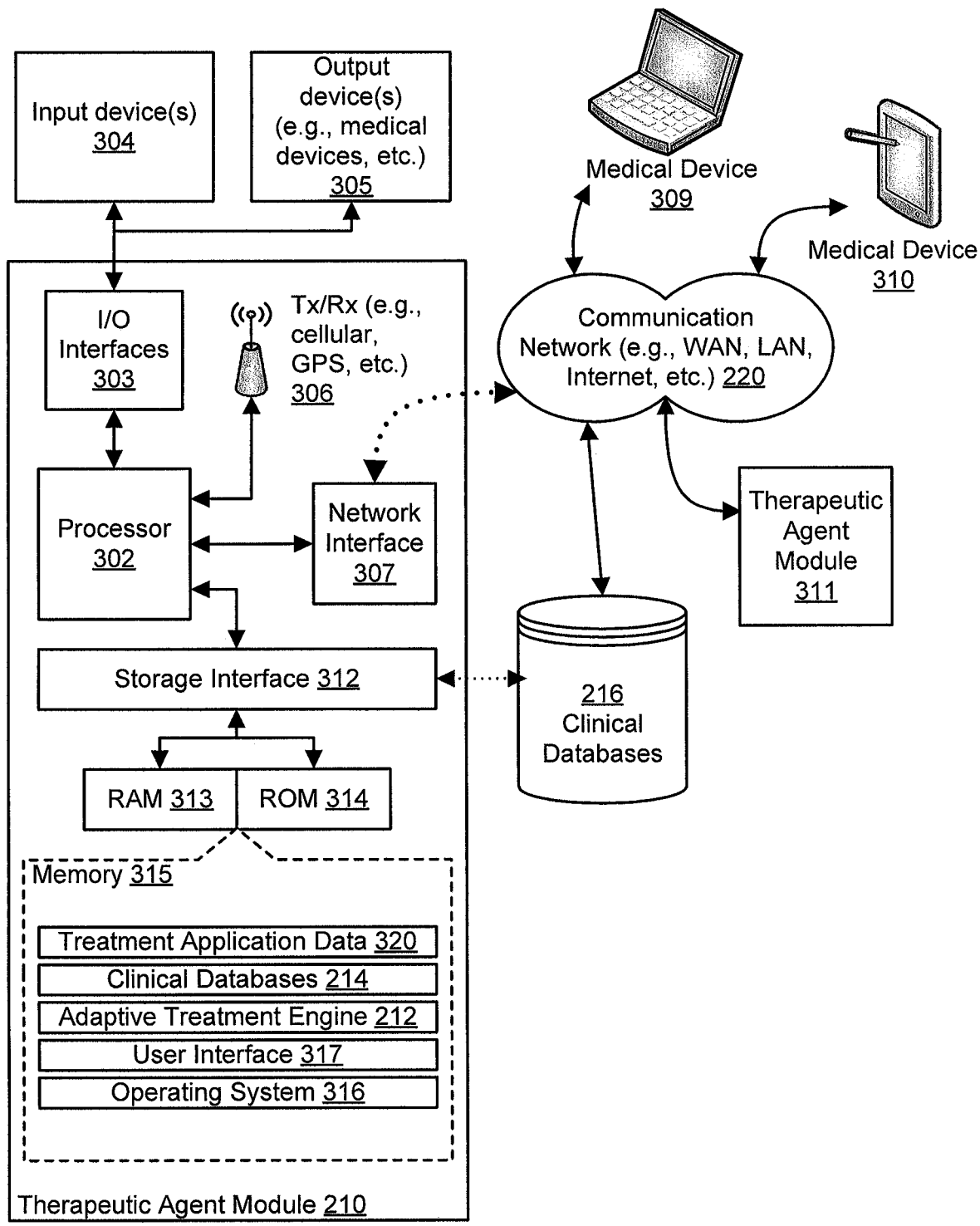
FIG. 3 is a block diagram of an exemplary therapeutic agent, in accordance with some embodiments of the present disclosure.

Therapeutic agent module 210 may be configured to provide adaptive radiotherapy using adaptive treatment engine 212 and clinical databases 214. For example, in some aspects, therapeutic agent module 210 may be configured to receive data from a clinical subject 218, which may include one or more medical devices (e.g., medical devices 309 and 310 as shown in FIG. 3). The therapeutic agent module 210 may also be configured to correlate the information to known treatment protocols, treatment tasks, and other information saved in clinical databases 214, clinical database 216, and/or other sources of data, and use the correlated information in the treatment of the patient. The therapeutic agent module 210 may retain the correlated information in clinical databases 214. Further, therapeutic agent module 210 may include a data management system that includes an adaptive treatment engine 212 and one or more clinical databases 214, which contain patient data, a library of standardized radiotherapy protocols, and a library of therapeutic tasks cross-correlated with various aspects of the protocols.

Therapeutic agent module 210 may process diagnostic information from clinical subject 218 during the treatment of a patient such as, for example, one or more medical images acquired by an imaging medical device (e.g., CT, MR, PET, SPECT, X-ray, Ultrasound, and the like), and save the medical image(s) to one or more records in clinical databases 214. The therapeutic agent module 210 may obtain the medical image(s) from clinical database 214, analyze the medical image(s), and select a plurality of therapeutic protocols from the clinical database based on the analysis of the medical image(s). Analysis may include determination of bladder full/empty, detection of bowel gas, shrinkage of the primary tumor site, and retraction of organs for example, among others. The therapeutic protocols, which are discussed hereafter in further detail, may be selected based on the medical image(s) and other information, such as, for example, reference protocol data, which are model recipes for radiotherapy treatment.

The selection performed by the therapeutic agent module 210 may be based on any given number of calculations (e.g., thousands, millions or billions of calculations) performed by a processor (e.g., an accelerated processing unit (APU) or a hybrid CPU/GPU processor, processor 302 as described below, and the like) in a short period of time. In some aspects, the therapeutic agent module 210 may be configured to perform predictions of specific therapeutic responses on hundreds of potential treatment options based on large data sets obtained from clinical subject 218 and clinical databases 214. According to some embodiments, the therapeutic agent module 210 may be configured to develop a first treatment plan from the plurality of therapeutic protocols, and, during a simulated delivery of the first treatment plan, evaluate intermediate data including acquired images and calculated doses. The evaluation may indicate an altered patient state due to the simulated course of execution of the first treatment plan, and as a result, select a second treatment plan using a second plurality of therapeutic protocols based on reference protocol data and adaptive protocol data.

Therapeutic agent module 210 may provide adaptive radiotherapy to the clinical subject 218 using information saved on the clinical databases 214 physically located on or proximate to the therapeutic agent module 210. According to other embodiments, therapeutic agent module 210 may use information saved on the clinical databases 216, which may be located locally within the same clinic or located remotely at another location and accessible over a network (e.g., communication network 220). Therapeutic agent module 210 may work in conjunction with other therapeutic agent modules 222, 224 and/or 226, which may be located in the same room, in the same clinic, or remotely located in another location. Therapeutic agent modules 222, 224, and 226 may share information in one or more common clinical databases (e.g., clinical databases 216) and/or maintain local copies of clinical databases on each of their respective local databases (e.g., 214 with respect to therapeutic agent module 210). According to other exemplary embodiments, clinical database 214 may be configured to retain redundant storage of one or more of any other operatively connected database. Accordingly, in the event of a connection failure to a remotely located database during the course of a treatment session, adaptive treatment engine 212 may access a local copy of the needed information from the clinical databases 214 to maintain the integrity of the clinical treatment in progress.

FIG. 3 is a block diagram of an exemplary therapeutic agent module 210 for implementing embodiments consistent with the present disclosure. Variations of therapeutic agent module 210 may be used for implementing one or more medical devices (e.g., medical devices 416, 418, and 420, shown in FIG. 4), medical device interface 420, and/or auxiliary device 415. Medical devices may include, for example, imaging devices that include image sensors for capturing images of a patient and therapeutic delivery devices for administering treatments (e.g., therapeutic radiation doses) to a patient. Medical devices are further discussed with respect to FIG. 4. Therapeutic agent module 210 may comprise a processor 302 (e.g., central processing unit ("CPU"), graphics processing unit ("GPU"), application specific integrated circuit ("ASIC"), and the like). Processor 302 may comprise at least one data processor for executing computer-executable program instructions, executing computer program components, executing user-requests or system-generated requests. A user may include a person using a medical device such as, for example, a medical professional 424 (e.g., a physician, a nurse, a therapist, a medical technician, a radiologist, an oncologist, or anyone with any medical training). The processor 302 may include specialized processing units such as integrated system (bus) controllers, memory management control units, floating point units, graphics processing units, digital signal processing units, etc. The processor 302 may include a microprocessor, such as AMD Athlon, Duron or Opteron, ARM's application, embedded or secure processors, IBM PowerPC, Intel's Core, Itanium, Xeon, Celeron or other line of processors, etc. The processor 302 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), Systems on a Chip (SoC), etc.

Processor 302 may be disposed in communication with one or more input/output (I/O) devices via an I/O interface 303. The I/O interface 303 may employ communication methods and/or protocols (which are distinct from medical protocols as described herein) such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 303, therapeutic agent module 210 may communicate with one or more I/O devices. For example, the input device 304 may include a keyboard, mouse, joystick, camera, bar code reader, dongle, biometric reader, microphone, touch screen, touchpad, trackball, sensor (e.g., accelerometer, light sensor, RF detector, gyroscope, proximity sensor, or the like), stylus, scanner, storage device, transceiver, video device/source, etc.

Figure 4:
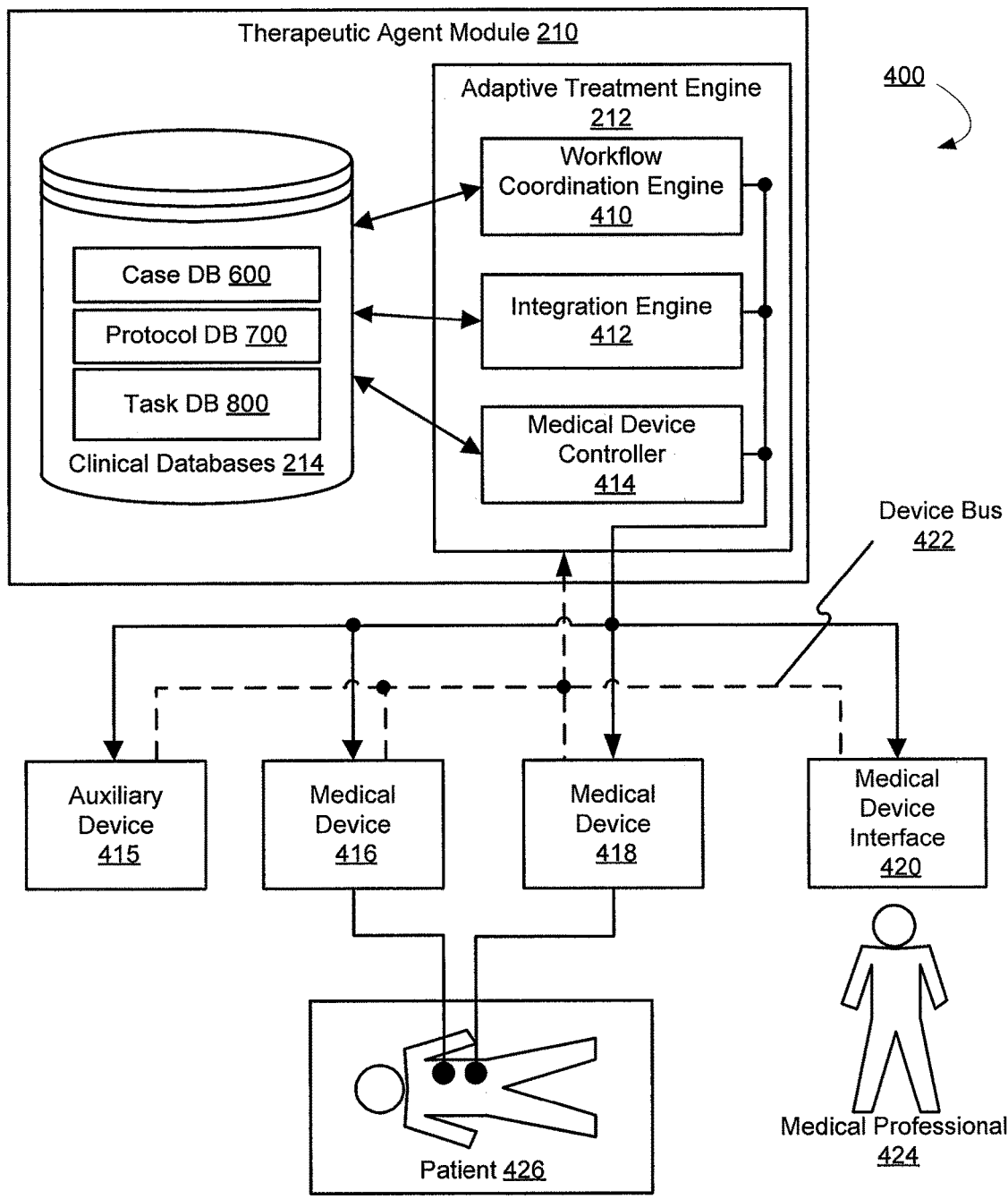
FIG. 4 is a functional block diagram of an exemplary adaptive radiotherapy treatment management system, according to some embodiments of the present disclosure.

Input device 304 may also be one or more medical devices such as, for example, medical devices 416, 418, and/or 420 (as depicted in FIG. 4). As stated above, medical devices 416, 418, and/or 420 may be a brachytherapy system, an afterloader, a linear accelerator, a magnetic resonance scanner combined with a linear accelerator, or other therapeutic medical system.

Output device 305 may be a printer, fax machine, video display, audio speaker, etc. In some embodiments, a transceiver 306 may be disposed in connection with processor 302. Transceiver 306 may facilitate various types of wireless transmission or reception. For example, transceiver 306 may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, processor 302 may be disposed in communication with communication network 220 via a network interface 307. Network interface 307 may communicate with communication network 220. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. Communication network 220 may include, without limitation, a direct interconnection, local area network (LAN), wide area network (WAN), wireless network (e.g., using Wireless Application Protocol), the Internet, etc. Using network interface 307 and communication network 220, the therapeutic agent module 210 may communicate with devices 309 and 310, and/or with therapeutic agent 311. As shown in FIG. 3, these devices 309 and 310 may include, without limitation, personal computer(s), server(s), various mobile devices such as cellular telephones, smartphones (e.g., Apple iPhone, Blackberry, Android-based phones, etc.), tablet computers, laptop computers, notebooks, handheld medical devices, and the like. In some embodiments, the therapeutic agent module 210 may itself embody or be stored on one or more of these devices, 309 or 310.

In some embodiments, processor 302 may be in communication with one or more memory devices (e.g., RAM 313, ROM 314, etc.) via a storage interface 312. The memory devices may include memory 315 (e.g., non-transitory computer readable medium) configured to store data or information (e.g., programs) associated with one or more of treatment application data 320, clinical databases 214, adaptive treatment engine 212, user interface 317, and operating system 316. Storage interface 312 may also be configured to connect with other devices including, without limitation, one or more external databases such as clinical databases 216, memory drives, removable disc drives, etc., employing connection protocols such as serial advanced technology attachment (SATA), integrated drive electronics (IDE), IEEE-1394, universal serial bus (USB), fiber channel, small therapeutic agent modules interface (SCSI), network attached storage, iSCSI, etc. The memory devices may also or alternatively include one or more of a drum, magnetic disc drive, magneto-optical drive, optical drive, redundant array of independent discs (RAID), solid-state memory devices, solid-state drives, etc. Variations of memory devices may be used for implementing, for example, clinical databases 214, and other databases discussed below (e.g., clinical databases 216, case databases 600, protocol databases 700, and task database 800). In an embodiment the memory devices may include random access memory (RAM), static random access memory (SRAM), synchronous dynamic random access memory (SDRAM), Double Data Rate SDRAM (e.g., DDR3 and memory specified to support DDR3 1333 standard, and the like), and Rambus DRAM (RDRAM). The memory devices may be configured in many ways, for example, as single in-line memory modules, dual in-line memory modules, or removable RAM memory, and the like. Such memory devices may be employed to store diagnostic information from a particular patient, e.g., medical images, and two or more treatment plans in order to reduce the number of fetches of such data from a database and thereby speed the operation of the processes as described herein.

The memory devices may store a collection of program or database components that may relate to, without limitation, adaptive treatment engine 212, clinical databases 214, an operating system 316, user interface 317, and treatment application data 320 (e.g., any data variables or data records discussed in this disclosure), etc. Operating system 316 may facilitate resource management and operation of the therapeutic agent module 210. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 317 may facilitate display, execution, interaction, manipulation, or operation of program components through textual or graphical facilities (e.g., graphical user interfaces). For example, user interfaces may provide computer interaction interface elements on a display system operatively connected to the therapeutic agent module 210, such as cursors, icons, check boxes, menus, scrollers, windows, widgets, etc. Graphical user interfaces (GUIs) may be employed, and may include, for example, without limitation, Apple Macintosh operating systems' Aqua, IBM OS/2, Microsoft Windows (e.g., Aero, Metro, etc.), Unix X-Windows, web interface libraries (e.g., ActiveX, Java, JavaScript, AJAX, HTML, Adobe Flash, etc.), or the like.

According to some embodiments, therapeutic agent module 210 may implement a web browser stored program component (not shown). The web browser may be a hypertext viewing application, such as, for example, Microsoft Internet Explorer, Google Chrome, Mozilla Firefox, Apple Safari, or any software application providing connection to the internet allowing hypertext viewing. Secure web browsing may be provided using HTTPS (secure hypertext transport protocol), secure sockets layer (SSL), Transport Layer Security (TLS), etc. Web browsers, for example, may utilize facilities such as AJAX, DHTML, Adobe Flash, JavaScript, Java, application programming interfaces (APIs), etc.

Clinical databases 214 and 216 may be implemented as fault-tolerant, relational, scalable, secure databases, or any combination thereof, for example, such as Oracle or Sybase. Clinical databases 214 and 216 may include various architectures based on its implementation. Clinical databases 214 and 216 may be implemented using standardized data structures, such as an array, a hash, a linked list, a struct, a record, a structured text file (e.g., XML), a table, or the clinical databases 214, 216 may be implemented as object-oriented databases (e.g., using ObjectStore, Poet, Zope, etc.). Clinical databases 214 and 216 may be implemented using a combination of relational and unstructured data. Clinical databases 214 and 216 may be consolidated or distributed, sometimes among the various therapeutic agent modules discussed above in this disclosure. It is to be understood that the structure and operation of any computer or database component may be combined, consolidated, or distributed in any working combination. In an embodiment, data elements may contain pointers to one or more additional databases, thereby introducing a redirection level for the adaptive radiotherapy treatment management system 400. For example, clinical databases 214 and 216 may contain provenance graphs relating data in one structure or system to data in another structure or system. Such redirection by the plurality of nodes may typically not be observable by an end user.

FIG. 4 is a functional block diagram of an exemplary adaptive radiotherapy treatment management system 400, according to some embodiments of the present disclosure. System 400 may include the therapeutic agent module 210, medical devices 416 and 418, a medical device interface 420, and an auxiliary device 415. Therapeutic agent module 210 may be operatively connected to medical devices 416 and 418. Medical device interface 420 may be connected to and configured to control the medical devices 416, 418, and the auxiliary device 415. The medical device interface 420, the medical devices 416 and 418, and the auxiliary device 415 may be connected via a device bus 422.

Medical device 416, and optionally 418, may be any device used in the radiotherapy treatment of patient 426. In an exemplary embodiment, medical device 418 is not required, but if present, is different from medical device 416. For example, medical device 416 may be a brachytherapy afterloader while device 418 is a linear accelerator. Further, medical devices 416 and 418 may include a brachytherapy delivery system, a brachytherapy US-guided needle insertion system, a gated brachytherapy delivery configuration, a brachytherapy device configured as predictive tracking delivery configuration, an afterloader, an imaging device, a robotic system, a gamma knife, endoscopic equipment, a linear accelerator, a combined MRI-linear accelerator, etc. Medical devices 416 and 418 may be configured to receive information from and provide information to therapeutic agent module 210.

According to some embodiments, medical device 416 may be an imaging device that includes one or more image forming capabilities for capturing images of a patient anatomy and/or for providing large datasets of machine-readable image information. For example, the medical device 416, may be a CT scanner, a PET scanner, a MRI scanner, a SPECT scanner, or any type of device that can be used for medical imaging a patient's anatomy.

In other examples, medical device 418 may be a brachytherapy afterloader configured to receive control commands from therapeutic agent module 210 in response to a treatment decision facilitated by or made by therapeutic agent module 210.

In other embodiments, medical device 416 may be an MRI scanner while medical device 418 is a linear accelerator. Both receive control commands from the therapeutic agent module 210 via the medical device controller 414 and work in tandem to analyze the image data acquired by medical device 416 and adapt the delivery administered by medical device 418.

Medical device interface 420 may be configured to control medical devices 416 and 418 during the course of a treatment of patient 426. According to some embodiments, therapeutic agent module 210 may receive inputs and provide outputs to a user, such as, for example, a medical professional 424. Medical device interface 420 may be configured to send instructions to and receive instructions from auxiliary device 415, medical devices 416 and 418, and the therapeutic agent module 210. Medical device interface 420 may also be configured to control and/or communicate with auxiliary device 415. For example, medical device interface 420 may be configured to provide control to therapeutic agent module 210.

Auxiliary device 415 may be one or more non-medical devices providing non-medical functionality to system 400. For example, in some aspects auxiliary device 415 may perform various "service" algorithms such as, for example, a time-deterministic Monte Carlo algorithm, a Pareto optimization, a graphical processing unit (GPU) stack for the rapid execution of massive image reconstruction calculations, etc. Auxiliary device 415 may receive information from and provide information to therapeutic agent module 210 and/or medical device interface 420. Therapeutic agent module 210 may perform any one or more calculation steps described herein using auxiliary device 415.

Therapeutic agent module 210 may include the adaptive treatment engine 212, and may include one or more clinical databases 214. Clinical databases 214 may include a plurality of databases including a case database 600, a protocol database 700, and task database 800, which are discussed in further detail below. Clinical databases 214 may provide information to and receive information from adaptive treatment engine 212.

Adaptive treatment engine 212 may include a medical device controller 414, an integration engine 412, and a workflow coordination engine 410. Adaptive treatment engine 212 may be configured to execute defined activities in operatively connected devices such as, for example, an imaging device (e.g., medical device 416). In some embodiments, the adaptive treatment engine 212 may parse the clinical databases 214 in real time (e.g., real time in this context means that parsing is performed during a treatment session while the treatment engine 212 is in use) to determine correlations between vast datasets and to determine candidate protocols, and/or protocol fragments, and tasks in the universe of options given a particular set of circumstances learned through parsing the databases. For example, the adaptive treatment engine 212 may determine, by using the correlations during a treatment fraction delivery session, whether previously encountered cases were similar in nature (e.g., in terms of movement dynamics and/or structure set elements, such as relative location and size), and the adaptive treatment engine 212 may determine an optimal approach to the current case. In other embodiments, adaptive treatment engine 212 may coordinate a variety of therapeutic processes managed by therapeutic agent module 210. Therapeutic agent module 210 may be configured to optimize system 400 behavior based on dynamically changing clinical circumstances (e.g., patient response to a particular treatment during a treatment session). In some examples, adaptive treatment engine 212 may be configured to continually update clinical databases 214 with clinical response and efficacy information for a future clinical treatment.

Adaptive treatment engine 212 may automatically access, analyze and formulate treatment plans based on large bodies of data (e.g. diagnostic information) stored in clinical databases 214. For example, after parsing case database 600 and protocol database 700, adaptive treatment engine 212 may determine (e.g., via processor 302) that, based on diagnostic information, in this case medical image data obtained via medical device controller 414 and processed via integration engine 412, there is a 94% probability that a particular protocol will be effective at reaching a particular clinical objective given the circumstances determined from the medical image. For example, the medical image might reveal an anatomy (e.g. changes in bladder/bowel/rectum filling) suitable to deliver extra radiotherapy dose to the target while not compromising the dose to the surrounding OAR, even though the protocol, for example, predicts that the dose to the target should be reduced due to the possibility of overdose to the OAR. In this way, adaptive treatment engine 212 can provide clinical decision support that would allow comparisons of expected efficacies of different optional treatment modalities applied to the same patient geometry, in terms of the expected delivered dose to various elements of the structure set (e.g., OAR and/or target tumor) and/or in terms of expected outcomes for the various considered options. Adaptive treatment engine 212 may analyze the medical image to discern clinically meaningful data points for cross-correlation, and parse clinical databases 214 to find likely correlation between other instances of the particular protocol used in previous treatment plans for the same patient, or even across different patients, that showed positive tumor response (e.g. shrinkage) given the circumstances determined from the image. Adaptive treatment engine 212 may access task database 800 to determine clinically allowable tasks in connection with a candidate protocol, and the particular protocol to a qualified authority (e.g., medical professional 424) as part of a plurality of treatment options for comparison. Accordingly, adaptive treatment engine 212 may be configured to analyze data from the ever increasing archive of correlated data stored in, for example, the case database 600, the protocol database 700, and the task database 800 in order to perform large numbers of comparisons (e.g., thousands, millions, etc.) using processor 302 to provide clinically allowable tasks for patient 426. Adaptive treatment engine 212 may perform these exemplary actions in a matter of moments (e.g., within several seconds, such as between 1 and 10 seconds). In any case, the actions can be performed within a practical time scale. Practicality depends on the value of the result weighed against the cost of waiting for it.

In some embodiments, adaptive treatment engine 212 may perform large numbers of comparisons of diagnostic information (e.g., image data, protocol comparisons, task correlations, and the like) in real time, and use the comparisons and correlations to select clinically superior treatment options for patient 426. According to some embodiments, adaptive treatment engine 212 may provide to the medical professional 424 correlations learned during an ongoing treatment or sets of comparable treatments in a human-readable format, determine the efficacy of the candidate protocol given the observed and recorded clinical circumstances, and determine an efficacy of the treatment after it is delivered to patient 426. In one example, adaptive treatment engine may cross-reference the efficacy to the appropriate data structures in the clinical databases 214 (e.g., data structures discussed in more detail with respect to FIGS. 6, 7, and 9).

Adaptive treatment engine 212 may include learning algorithms such as Support Vector Machine (SVM), Adaboost/Logitboost, Random Forests, deep learning, and/or Neural Networks, among others. In some examples, adaptive treatment engine 212 may increase its clinical intelligence over time by learning from new correlations made from data incorporated into therapeutic agent module 210.

In this way, medical professional 424 may benefit from the information learned and remembered by adaptive treatment engine 212. Medical professional 424 may also be able to share the information in a meaningful format, via system 400, with another physician (not shown) treating a patient with similar circumstances that may point to the particular protocol. Regardless of whether the second physician is treating the same patient 426 at a later date, or contemporaneously treating a different patient with a substantially similar physiological condition or situation, the second physician can use the learned knowledge (e.g., in real time) to the benefit of the patient.

Figure 5:
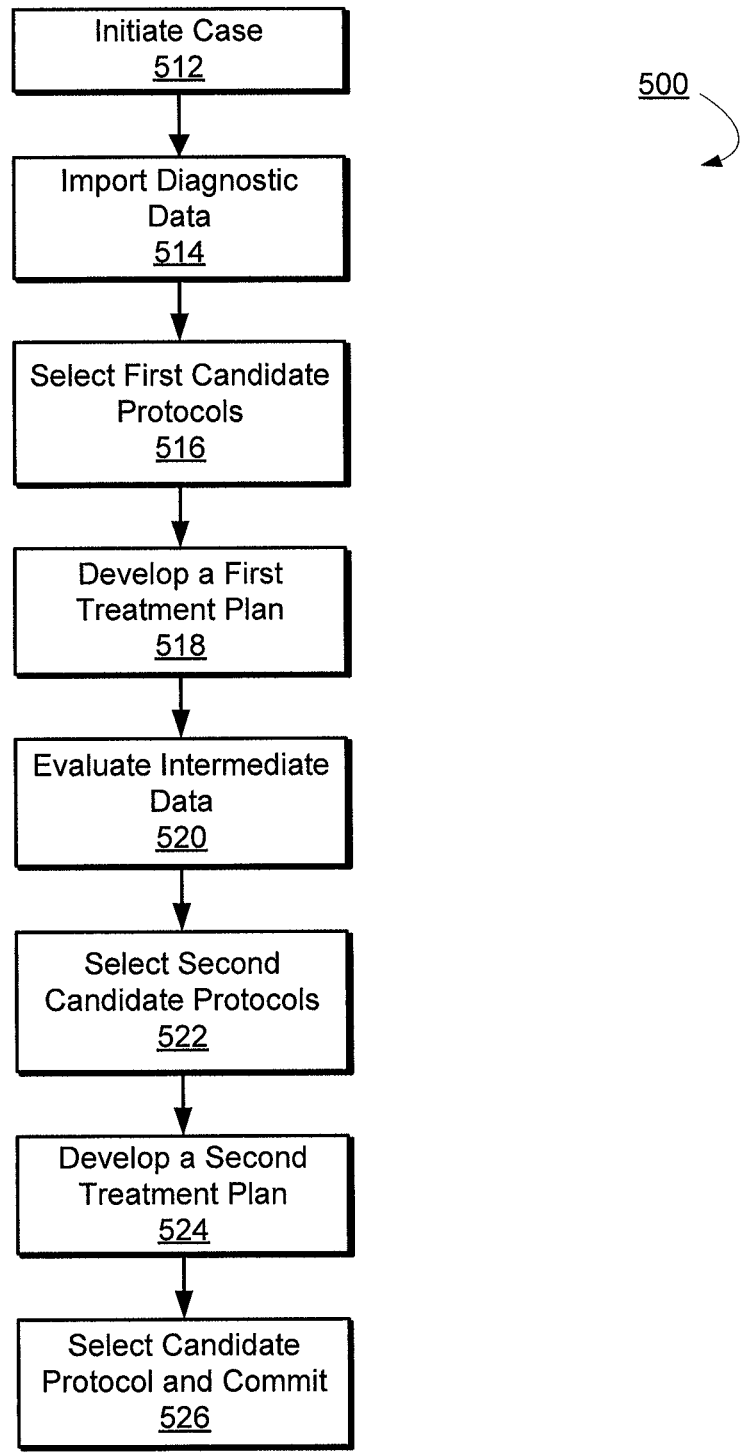
FIG. 5 is a flow diagram illustrating an exemplary method for adaptive cancer treatment, in accordance with some embodiments of the present disclosure.

FIG. 5 shows an exemplary method for adaptive radiotherapy treatment 500 (e.g., cancer treatment), according to some embodiments of the present disclosure.

At Step 512, the adaptive treatment engine 212 may initiate a new case in response to user input. For example, medical device controller 414 may receive an instruction provided by medical device interface 420 indicative of a radiotherapy treatment initiated for patient 426. Adaptive treatment engine 212 may access the case database 600 to create a case record, as described below. In some embodiments, treatment engine 212 may determine that data is required in order to select a protocol and that medical image data is also required. Accordingly, treatment engine 212 may initiate an "import" task.

At Step 514, diagnostic information is imported. In some embodiments, medical device controller 414 may retrieve image data (not shown) from medical device 416. For example, medical imaging device 416 may perform one or more image processing operations to obtain an image of the patient, which is then imported by medical device controller 414. The import task may be one task in a plurality of tasks saved in the task database 800. The integration engine 412 may consider diagnosis information learned from import and analysis of the image data, access medical device configuration 724 from protocol database 700, and/or execute one or more tasks from task database 432 to prompt for and receive user input. In other embodiments a combination of more than one dataset/modality may be used to obtain a balanced view on the case.

According to some embodiments, adaptive treatment engine 212 may analyze the imported image data to discern clinically useful information. In particular, processor 302 may execute one or more treatment application data 320, which may access reference data (e.g., data contained in one or more of databases 600, 700, and 800) during the analysis. Those skilled in the art should appreciate that a wide variety of medical images and/or other diagnostic information (e.g., clinical data such as blood or other fluid tests, radiology tests, biopsies, etc) may be imported by adaptive treatment engine 212. Although embodiments described herein do not indicate any particular analysis of the medical image and/or diagnostic information, it should be appreciated that an analysis of an imported medical image may include any one or more known analyses known and commonly used in the art. For example, image analysis may include automatic contouring, segmentation, analysis of "dynamic contrast enhanced" data sets, physiological response assessment, among other analyses.

At Step 516, adaptive treatment engine 212 may select a first plurality of therapeutic protocols from the clinical databases 214, where the selection is based on the imported medical image and reference protocol data.

At step 518, adaptive treatment engine 212 may develop a first treatment plan using the selected protocols in view of a clinical objective. According to some embodiments, adaptive treatment engine 212 may present the plurality of options to medical professional 424 in an easily-understood format that provides only the necessary information for making a clinical decision. For example, the thousands or even millions of machine-readable data points considered by adaptive treatment engine 212 may be distilled down to a number of factors, such as dose conformance, tumor control probability, normal tissue complication probability, biologically equivalent dose to structures, outcome uncertainty, and the like, and displayed on output device 305. Adaptive treatment engine 212 may execute a task requesting input indicative of a treatment plan selection, and receive user input via input device 304. The input may indicate a treatment decision for patient 426. According to some embodiments, medical professional 424 may allow adaptive treatment engine 212 to select the treatment protocol. For example, a clinically accepted rule may link a particular protocol, out of the selected protocols, to an expected outcome of treatment for the patient, and the set of selected protocols may provide a sufficient basis for that the linkage.

At Step 520, adaptive treatment engine 212 may evaluate the intermediate data by determining, based on medical device configuration 724, quality assurance guidelines 722, clinical objective(s) 630 and/or 632, and other data. Intermediate data may be collected and/or generated by adaptive treatment engine 212 when the selected protocol is delivered to patient 426, via medical devices 416, 418, and/or auxiliary device 415.

At Step 522, adaptive treatment engine 212 may select a second plurality of candidate protocols based on the evaluation of intermediate data.

At Step 524, adaptive treatment engine 212 may develop a second treatment plan based on the selected second plurality of candidate protocols. It is contemplated that more than two alternative treatment plans may be selected.

At Step 526, adaptive treatment engine 212 may select a desired treatment (e.g., a second treatment plan) from the second plurality of candidate protocols and commit to the selection (e.g., deliver the treatment).

Figure 6:
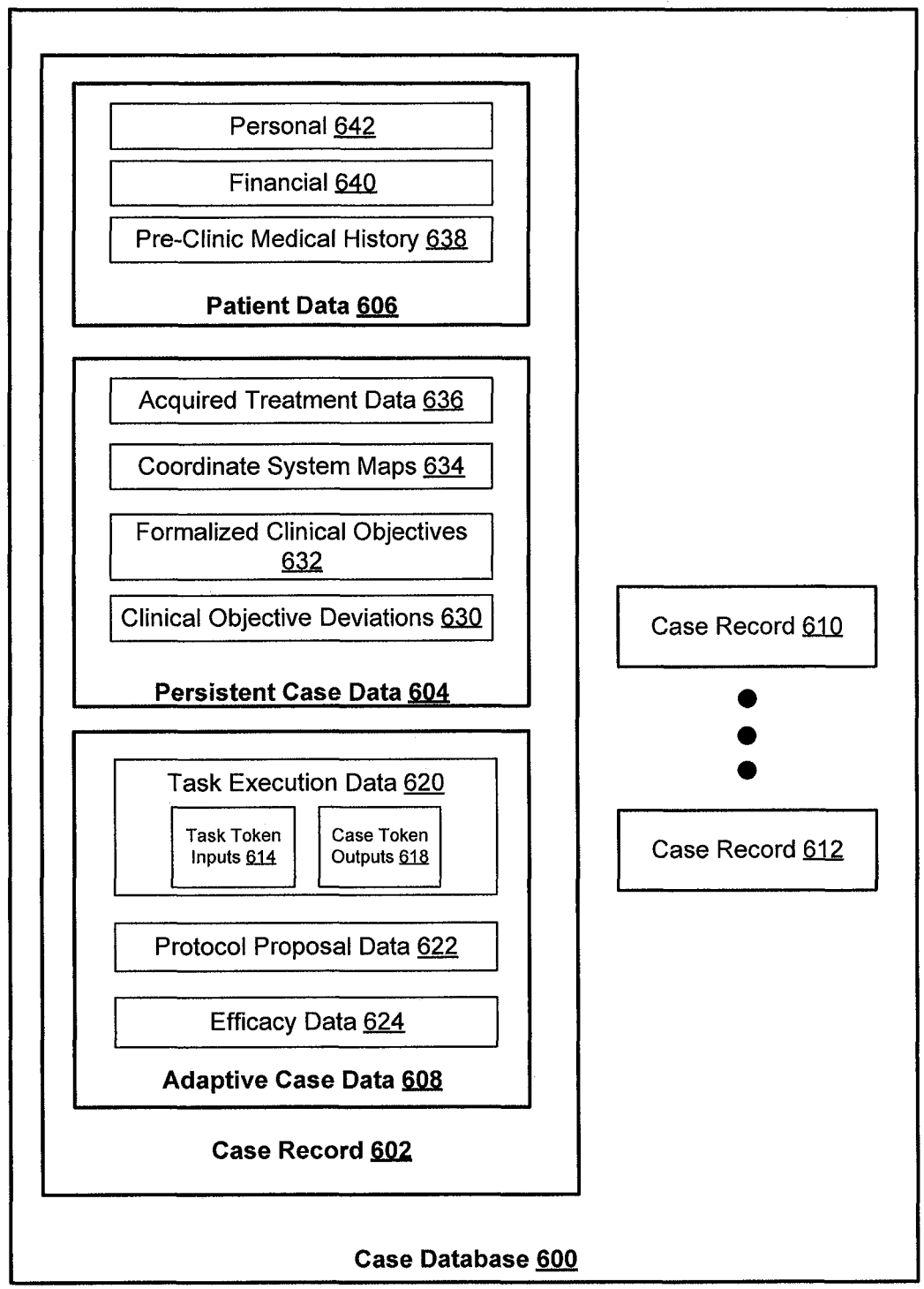
FIG. 6 is a block diagram of an exemplary adaptive radiotherapy case database, in accordance with some embodiments of the present disclosure.

FIG. 6 depicts a block diagram of an exemplary adaptive radiotherapy case database 600, in accordance with some embodiments of the present disclosure. The case database 600 may contain a plurality of case records including case records 602, 610 and 612. A case record may contain data sets that represent snapshots of patient information relevant to a clinical treatment (e.g., a case). These snapshots are called "model nodes." A model node may include information that connects a clinical objective (e.g., the goal set by medical professional 424 for a particular treatment) with a patient (e.g., patient 426). A case record may also associate data collected by medical device controller 414 with the clinical objective, associate, potential clinical treatments with delivered treatments, and associate the results for the delivered treatment with particular protocols executed by therapeutic agent module 210. In several ways, a case record may represent an overview of the evolution of the patient information relevant to a clinical treatment as the case is developed (e.g., as treatments are selected, delivered, and results are observed). According to some embodiments, case records may be stored in the case database 600.

Although three records are depicted in this example for the case database 600, it should be appreciated that case database 600 may contain any number of case records. Case database 600 may be a NoSQL/graph/object store database, such as, for example, Orient DB or Neo4J. The case database 600 may also be another type of database architecture known in the art. The case record 602 may include three general categories of case data, including adaptive case data 608, persistent case data 604, and patient data 606. The structure of the case record may be, for example, a directed non-cyclical graph.

Patient data 606 is a persistent record associated with a patient (e.g., patient 426) and may contain data structures for the patient's personal information 642, financial information 640, pre-clinical medical history 638, etc. Patient data 606 may be shared and maintained in parallel across multiple case records associated with a particular patient. For example, if case records 602, 610 and 612 are all cases involving patient 426, patient data 606 may exist in all three case records. Although patient data 606 is depicted having data structures 638, 640, and 642, it should be appreciated that a wide variety of patient data is commonly associated with a patient record. For example, although not shown, patient data may include additional biographical and other information associated with patient 426.

Case record 602 may also include persistent case data 604. A case describes one or more courses of treatment administered to patient 426. Case data that is persistent may be shared across multiple case records. For example, persistent case data 604 may include acquired treatment data 636, which may include treatment data associated with previous treatments (e.g., cases, treatment fractions, radiotherapy treatments, and the like) administered by therapeutic agent module 210, and/or treatments from other systems and/or clinics (e.g., chemotherapy, surgery, etc.). Acquired treatment data 636 may include the data itself or contain links to persistent treatment data saved in case database 600 that may be associated with another case (and thus, another treatment). Acquired treatment data 636 may also include a plurality of links to previous case records (e.g., case record 608 and 610), which may be cross-correlated by adaptive treatment engine 212.

Persistent case data 604 may include coordinate system maps 634 providing coordinate system mapping information, including quantified uncertainty of data associated with a particular mapping. For example, data may be oriented from one point in space in system A and may be oriented in a different point in space when the data from system A is translated to system B. Accordingly, translating between coordinate systems (e.g., coordinate system for system A and coordinate system for system B) requires knowledge of the source coordinates, and would require a translation and a rotation to migrate from system A to system B, or visa-versa. Each system may have with it a particular quantified uncertainty quotient (e.g., an uncertainty matrix). Therefore, one or more correlation coefficients may be associated with each particular coordinate system mapping. In an embodiment, the one or more correlation coefficients may include a quantification of the uncertainty of the coefficients.

Persistent case data 604 may also include information regarding formalized clinical objectives 632. Formalized clinical objectives may indicate standardized clinical objectives associated with one or more clinical conditions associated with the case. For example, if a particular melanoma is successfully treated when Test Q shows a reading of 3% or less, then a formalized clinical objective indicating the standardized clinical objective of "3% or less on Test Q" may be associated with persistent case data 604. In a further example, a deviation from the formalized clinical objective 632 may be required. Continuing the previous example, a deviation to expand the range (e.g., 3% to 5.5%) with respect to Test Q may be warranted. When deviations from standardized clinical objectives are determined to be necessary by medical professional 424, clinical objective deviations 630 may indicate a persistent record of the deviation. The deviation record may be parsed and cross referenced by integration engine 412 to create meaningful correlations with which therapeutic agent module 210 increases the available knowledge base.

In contrast to persistent case data 604, which contains a persistent record of the case, adaptive case data 608 may contain data structures that may change during the course of the case. For example, adaptive case data 608 may include task execution data 620, protocol proposal data 622, and efficacy data 624. Adaptive case data 608 may be copied and/or modified when task execution data 620, protocol proposal data 622, and/or efficacy data 624 are modified. Linking between different records of adaptive case data 608 is provided by task token inputs 614 and/or case token outputs 618, as further described below, and stored in case record 602. In other words, when a task is executed, a record of that execution event is saved, along with configuration and other control information (e.g., intent). Furthermore, any specific information provided to the task and information returned by the task is also recorded. The task execution data 620 can indicate dependencies between input and output data, to enable traceable identification (e.g., provenance maps) of data influenced by previous results. Thus, case record 602 may contain many model nodes with such interconnected information.

Task execution data 620 may include task information in the form of task tokens. Task tokens represent an exchange of information that correlates case specific information such as persistent case data and patient data with information from outside of the case space. The case space is the body of data maintained by therapeutic agent module 210 (e.g., clinical database 214) and represents the evolution of the managed case(s). During the execution of tasks, information from outside the case space, such as acquiring an image or receiving user input, may be obtained. For example, a treatment planning task may require parameters defining a specific treatment machine. These machine parameters are present outside of the case space, in possibly another database (e.g., clinical database 216). For example, a task token may include a model node that contains data acquired previously as part of acquired treatment data 636. As cases develop, adaptive treatment engine 212 may perform tasks and record the execution of the task as part of case record 602. Tasks associated data records may be immutable task tokens (e.g., fixed states that do not change), and/or changeable task tokens. For example, task tokens may be acquired, obtained, and saved data sets (CT scans, magnetic resonance imaging (MRIs), etc.), one or more formalized statements of one or more treatment objectives (e.g. dose prescription, dose volume histogram (DVH) requirements, etc.), observations of a patient state (e.g. well-being before a prescribed fraction, prostate specific antigen (PSA) readings, etc.), and/or one or more obtained structure set elements (e.g., tumor, organs at risk (OAR) delineation data, etc.), among others.

According to some embodiments, adaptive treatment engine 212 may reference task token inputs 614 (e.g., received task tokens), and produce case token outputs 618. The task token inputs 614 and case token outputs 618 may retain a persistent record of the inputs and outputs of information for indexing and cross correlating, which may increase computational speed to an adaptive treatment engine 212. For example, within case record 602, an indication that efficacy data 624 should be updated (e.g., after a treatment fraction is performed) can be indicated by a task token reflected in task token inputs 614. In this case, adaptive treatment engine 212 can copy and store adaptive case data 608 in case record 602, while task token inputs 614 is updated with the new information. Adaptive treatment engine 214 may then copy and modify the adaptive case data 608 with an indication in case token outputs 618 that efficacy data 624 is updated with the new information. In this way, the previous adaptive case data 608 is indexed and cross correlated to the current adaptive case data 608. Thus, case record 602 can contain several linked model nodes.

Adaptive case data 608 may further include information regarding treatment protocol proposals of candidate treatment protocols. A treatment protocol, discussed in further detail hereafter, is a course of treatment that is comprised of one or more tasks. A treatment protocol proposal may include one or more treatment protocols proposed by the adaptive treatment engine 212 for future treatment. Protocol proposal data 622 (e.g., information related to the protocol proposals), and the tasks associated with the treatment protocols, may be indexed and cross correlated by the adaptive treatment engine 212 to maintain a record of available treatment options at any given point in the treatment timeline.

Efficacy data 624 may record a persistent record of the effectiveness of a particular protocol or other treatment option. For example, if adaptive treatment engine 212 selects protocols A, B, and C, and treatment C is delivered (e.g., treatment C is predicted to be the most effective), adaptive treatment engine 212 may record the efficacy of treatment C in efficacy data 624. According to some embodiments, adaptive treatment engine 212 may parse database 600, correlate treatment C with circumstances surrounding the selection of protocols A, B, and C, and correlate the efficacy of treatment C with respect to those particular circumstances. For example, for brain tumor treatment, the dose to the optical nerve may differ between selected protocols A, B and C, and the most favorable protocol may be selected based on dosage, if other outcome related data is acceptable. Accordingly, efficacy data 624 may contain information pertaining to case record 602, for example, specific to patient 426, and may also contain links to case tokens associated with other patients (not shown).

Responsive to an instruction to initiate a case, integration engine 412 may search case database 600 to determine whether patient data 606 exists for the patient. If patient data 606 exists for patient 426, adaptive treatment engine 212 may create a case record 602, and associate patient data 606 with case record 602. Adaptive treatment engine 212 may also initiate one or more additional tasks to prompt input of additional needed patient information. For example, adaptive treatment engine 212 may determine that patient data 606 lacks a patient date of birth. Adaptive treatment engine may prompt medical professional 424 to input the patient's date of birth (DOB). Accordingly, adaptive treatment engine 212 may record a case token output 618, which records the request for user input. Adaptive treatment engine 212 may receive the input, save the data input to patient data 606, and record a task token input 614. In this way, indexing and correlation between changes in case record 602 is maintained.

Figure 7:
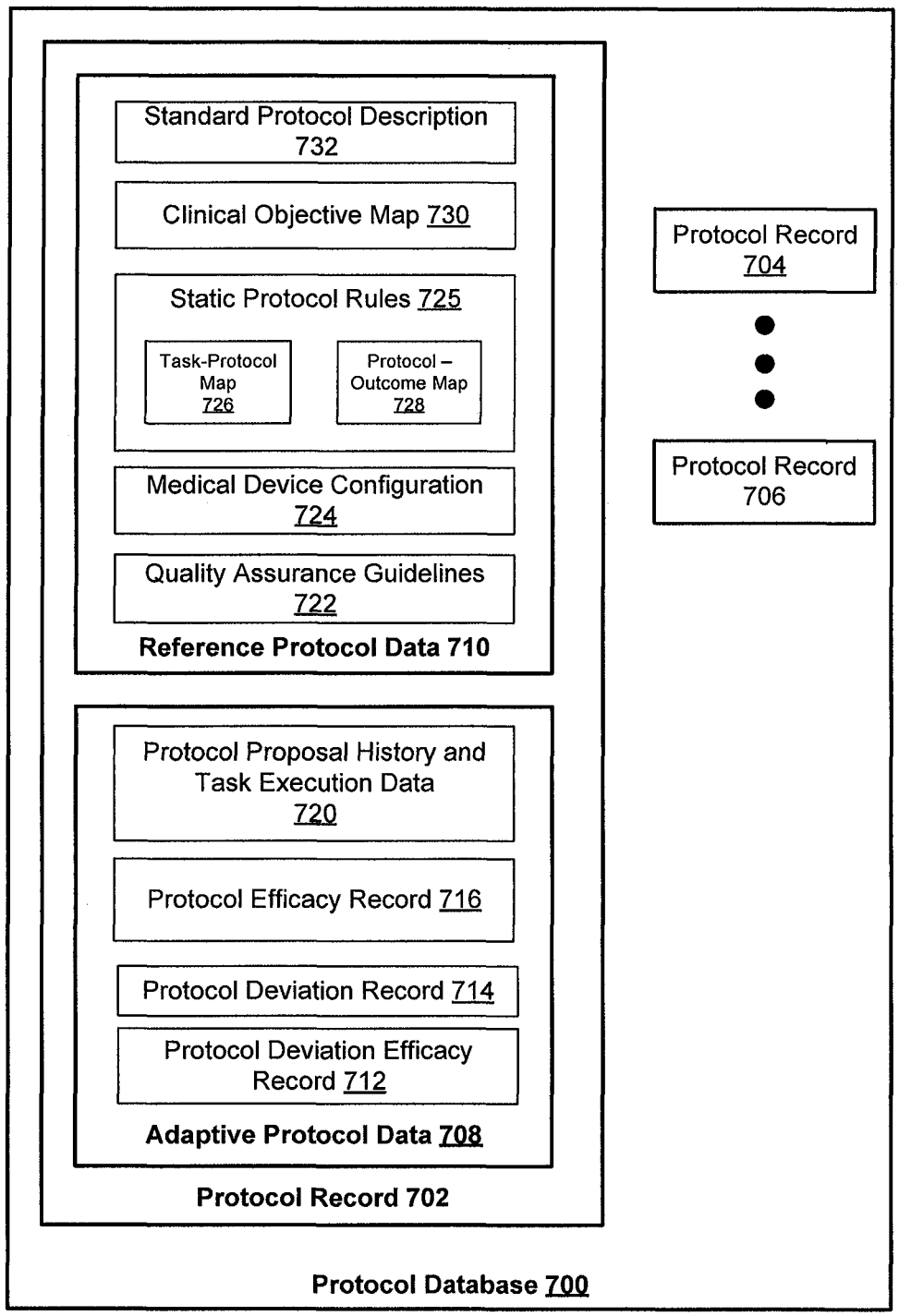
FIG. 7 is a block diagram of an exemplary adaptive radiotherapy protocol database, in accordance with some embodiments of the present disclosure.

FIG. 7 depicts a block diagram of an exemplary adaptive radiotherapy protocol database 700, in accordance with some embodiments of the present disclosure. The protocol database 700 may store protocol records 702, 704, and 706. Protocol database 700 may include any number of protocol records. Protocol database 700 may include data structures for protocol record 702 and reference protocol data 710. Protocol database 700 may be a case management model and notation (CMMN) type database such as, for example, a Camunda™ implemented database. Protocol database 700 may also utilize other database architectures known in the art.

Reference protocol data 710 may contain information particular to standard adaptive radiotherapy protocols used in the adaptive radiotherapy cancer treatment. Reference protocol data 710 may include standard protocol description 732, and a clinical objective map 730 linking the standard description to a particular clinical intent (e.g., formalized clinical objectives 632). Adaptive treatment engine 212 may cross reference static protocol rules 725 with one or more particular tasks from the task database 800. For example, if a typical protocol for a treatment fraction includes a task from the task record 802, information from that task record may be recorded and indexed in static protocol rules 725 as a task-protocol map 726. Outcomes referenced in protocol outcome map 824 may also be referenced in the respective protocol record at protocol outcome map 728.

Reference protocol data 710 may also include medical device configurations 724 and quality assurance guidelines 722. Quality assurance guidelines 722 may indicate one or more quantitative guidelines for administering the protocol referenced in protocol record 702.

Protocol record 702 may also contain adaptive protocol data 708. Similar to adaptive task data 808, adaptive protocol data 708 may include protocol information that is continually updated by adaptive treatment engine 212 over the course of one or more cases. Protocol record 702 may include protocol proposal history and task execution data 720, protocol efficacy record 716, protocol deviation record 714, and protocol deviation efficacy record 712.

Protocol proposal history and task execution data 720 may include a record of the cases (e.g., case record 602) with which the protocol associated with protocol record 702 has been proposed. For example, when the adaptive treatment engine 212 determines, based on the diagnosis derived from the medical image, that protocol 702 is one of three appropriate protocols to select in a treatment proposal for patient 426, adaptive treatment engine may reference the information in protocol proposal history and task execution data 720.

Protocol efficacy record 716, similar to efficacy data 624, may include information pertaining to an efficacy associated with protocol 702. When the standard protocol is changed (e.g., a deviation), the deviation may be recorded at protocol deviation record 714. Accordingly, when the deviated protocol is delivered, integration engine 412 may determine an efficacy of the treatment and record the efficacy data in 712.

Figure 8:
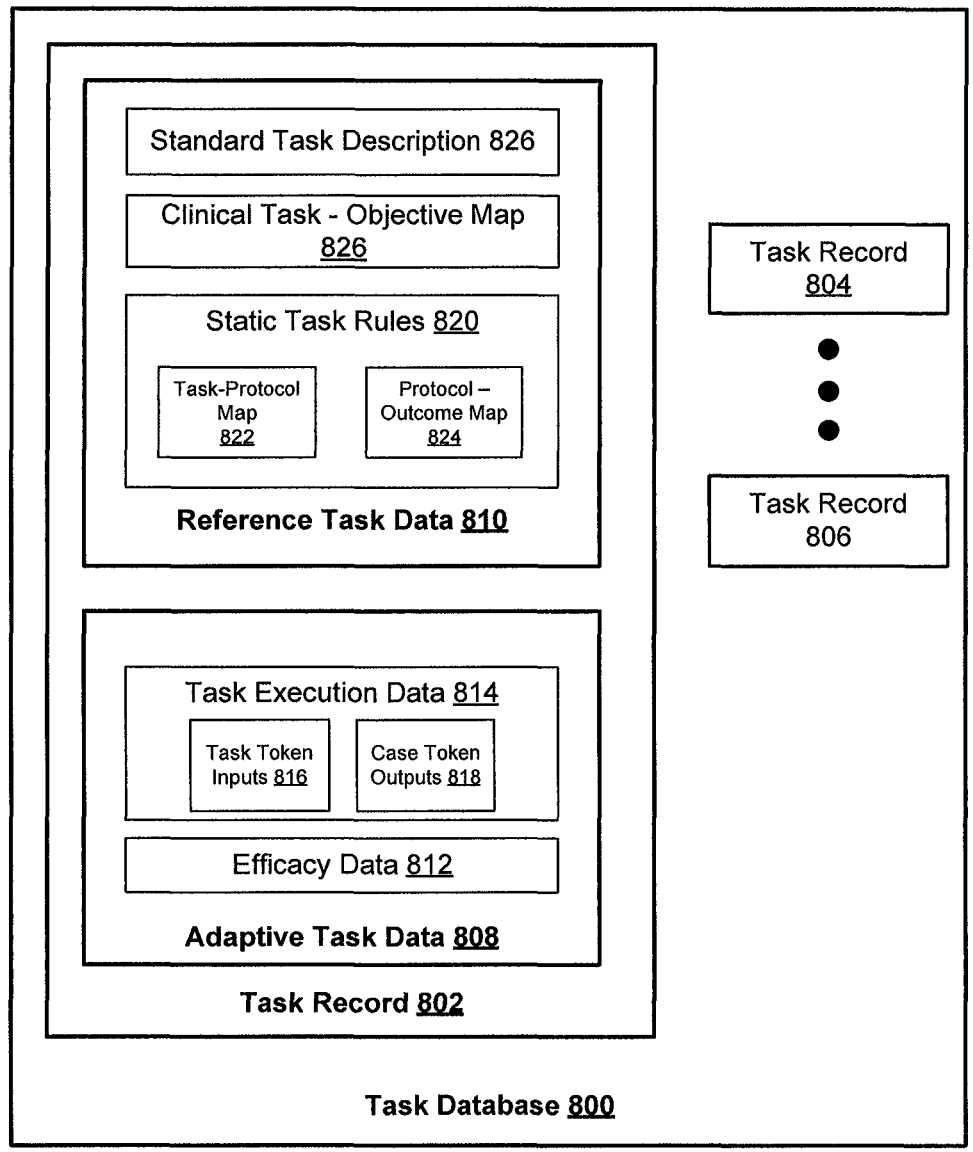
FIG. 8 is a block diagram of an exemplary adaptive radiotherapy task database, in accordance with some embodiments of the present disclosure.

Referring now to FIG. 8, a block diagram of an exemplary adaptive radiotherapy task database 800 is considered, in accordance with some embodiments of the present disclosure. The task database 800 may include a plurality of task records 802, 804 and 806. While the task database 800 depicts three task records, it should be appreciated that any number of tasks are stored in task database 800.

As previously discussed, a task is a saved step of a process (e.g., workflow), such as, for example, obtaining and saving acquired data sets, formalizing a treatment objective, determining a patient state, obtaining one or more structure set elements, control a medical device to administer a fraction, etc. A task may include a single step (e.g., input scan), or may include a plurality of steps (e.g., prompt user for data, import data, record to database, associate X with Y, send Y to medical device controller 414, etc.). Each task may be stored in the task database 800 as a task record 802.

The task record 802 may include adaptive task data 808 (described below) and reference task data 810. Reference task data 810 may include standard tasks associated with adaptive radiotherapy treatment with set tasks that are generally unchangeable. For example, reference task data 810 may include a setting for an adjustable control for medical device 418 that has only one safe setting in the context of the radiotherapy treatment. This "adjust control" task may be saved as a static task rule 820.

The information in static task rules 820 may include associations between commonly administered tasks and the clinical objectives for which the tasks are commonly executed. For example, if a clinical objective of "administer fraction" is always associated with a task X as a matter of course (e.g., "X" being any particular task), adaptive treatment engine 212 may index and record the association as a clinical task-objective map 826. When particular protocols are selected by adaptive treatment engine 212, one or more tasks associated with the protocol may be indexed in task-protocol map 822. Data associated with the outcome of the task may be recorded in protocol outcome map 824. For example, if task Y (e.g., "Y" being a different particular task) is statistically associated with an 80% success rate when used with a particular protocol, the correlation may be recorded as a protocol outcome map 824.

In contrast to reference task data 810, which may be standardized rules and associations assigned to a particular task, task record 802 may also include adaptive task data 808. Adaptive task data 808 may include task execution data 814, which may be altered according to a learned experience by the adaptive treatment engine 212. For example, when the adaptive treatment engine 212 determines that one or more tasks should be invoked, the adaptive treatment engine 212 may index the association between the particular task and the circumstances surrounding the need to invoke the task. This associative information may be saved as part of task execution data 814. For example, in a simple scenario, the adaptive treatment engine 212 may learn that medical device 418 uses information L, B, and J to determine a result. Adaptive treatment engine 212 may associate the tasks "Obtain L," "Obtain B," and "Obtain J" with a particular circumstance that indicates that the use of medical device 418 may be necessary. For example, in certain brain tumors, the use of a proton dose delivery device may be indicated, and certain MRI data may be needed to accurately plan for the delivery of the proton dose. According to some embodiments, the adaptive treatment engine 212 may determine, based on previous instances of the particular circumstance leading to the use of medical device 418 (e.g., tasks obtain L, obtain B, and obtain J) that the medical device will likely be needed in view of the presence of this particular circumstance, and create a record of the association in clinical task-objective map 826 associated with task record 802. The previous instances of the particular circumstance may be saved as task token inputs 816. In an embodiment, the metadata (e.g., a set of considered treatment intents) associated with the instances may also be saved as a task token input 816. As a further example, case token outputs 818 may include metadata associated with particular cases indicative of the learned task information. Efficacy data 812 may record the case outcomes associated with the learned task information. For example, efficacy data 812 may point to case-specific efficacy data 624 as a cross-correlation between the execution of the learned task and the relative success of the execution with respect to the clinical objective. If the particular case (e.g., case record 602) included a deviation from formalized clinical objectives 632, this information may be linked and indexed with efficacy data 812 to provide useable intelligence for future applications of adaptive task data 808.

Figure 9:
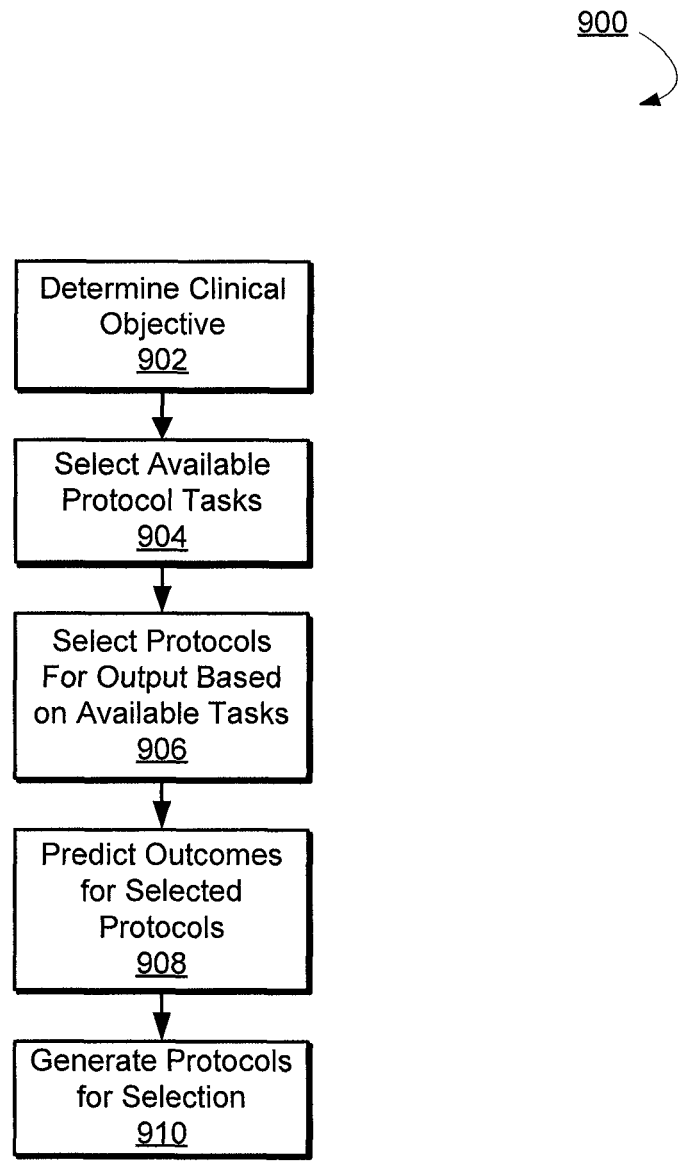
FIG. 9 is a flow diagram illustrating an exemplary method for selecting a first plurality of clinical protocols, in accordance with some embodiments of the present disclosure.

FIG. 9 depicts a flow diagram illustrating an exemplary method 900 for selecting a first plurality of clinical protocols, in accordance with some embodiments of the present disclosure.

At Step 902, the adaptive treatment engine 212 may first determine the clinical objective based on information analyzed from the medical image. For example, if the medical image, other diagnostic information, indicates a particular type of tumor near the surface of the skin, a clinical objective may be to measure the tumor and provide an adequate dose of radiation to reduce the tumor size by 80%.

At step 904, integration engine 412 may select available protocol tasks from task database 800 based on the diagnosis and/or analysis of the medical image. For example, integration engine 412 may determine a diagnosis L, and access static task rules 820 to determine from task-protocol map 822 that a particular set of tasks, for example, 11, 12, and 14, are appropriate for diagnosis L. Integration engine 412 may use available tasks 11, 12, and 14 to determine one or more protocols. The determination made by integration engine 412 may be determined by information accessed in a protocol database.

At Step 906, integration engine 412 may select candidate protocols for output based on the available tasks. The available tasks may be selected based on static task rules 820, which provide links in task-protocol map 822 between the protocol (e.g., protocol record 702) and the various tasks that are clinically acceptable for that protocol. Integration engine 412 may further analyze the selected protocols by predicting the outcomes for each candidate protocol.

At Step 908, integration engine 412 may predict clinical outcomes for the selected protocols (e.g., the extent to which each protocol is predicted to meet the stated clinical objective). Integration engine 412 may predict the outcomes in real time, based on available information including persistent case data 604, patient data 606, adaptive case data 608, reference protocol data 710 and/or adaptive protocol data 708. Predictions may be based, for example, on efficacy data 624 in association (correlated with) protocol proposal data 622, protocol deviation efficacy record 712 and other records indicating similar information as assimilated from protocol proposal history and task execution data 720.

At Step 910, integration engine 412 may generate protocols for selection. Generating the protocols may be based on the relative predictions made at Step 908, in view of formalized clinical objectives 632 and/or clinical objective deviations 630.

Figure 10:
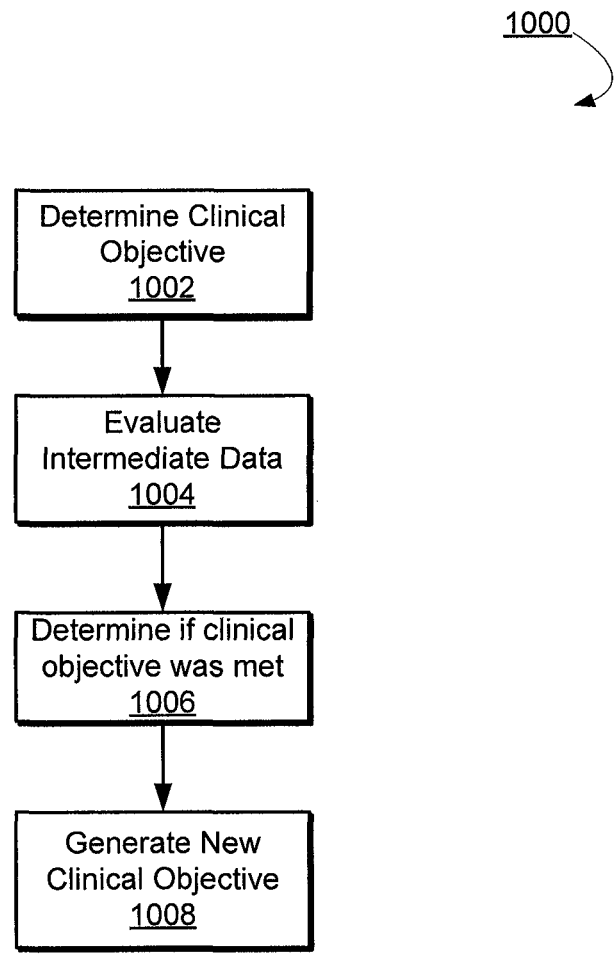
FIG. 10 is a flow diagram illustrating an exemplary method for evaluating intermediate data, in accordance with some embodiments of the present disclosure.

FIG. 10 shows a flow diagram illustrating an exemplary method for evaluating intermediate data 1000, in accordance with some embodiments of the present disclosure.

At Step 1002, integration engine 412 may determine the clinical objective from formalized clinical objectives 632 and/or clinical objective deviations 630.

At Step 1004, therapeutic agent module 210 may execute one or more tasks to analyze the intermediate data.

At Step 1006, integration engine 412 may determine from the analysis whether the clinical objective was met. If the clinical objective has been met, no adaptation to the treatment plan may be necessary.

At Step 1008, if the objective has not been met, adaptive treatment engine 212 may determine whether the clinical objective requires alteration. If no change is necessary (for example, the treatment goal was simply not met, but the goal was proper) treatment engine 212 may not alter the clinical objective. If a change in clinical objective is necessary, treatment engine 212 may prompt for a new clinical objective. According to some embodiments, treatment engine may generate the new objective independently and record the formalized clinical objectives 632.

Figure 11:
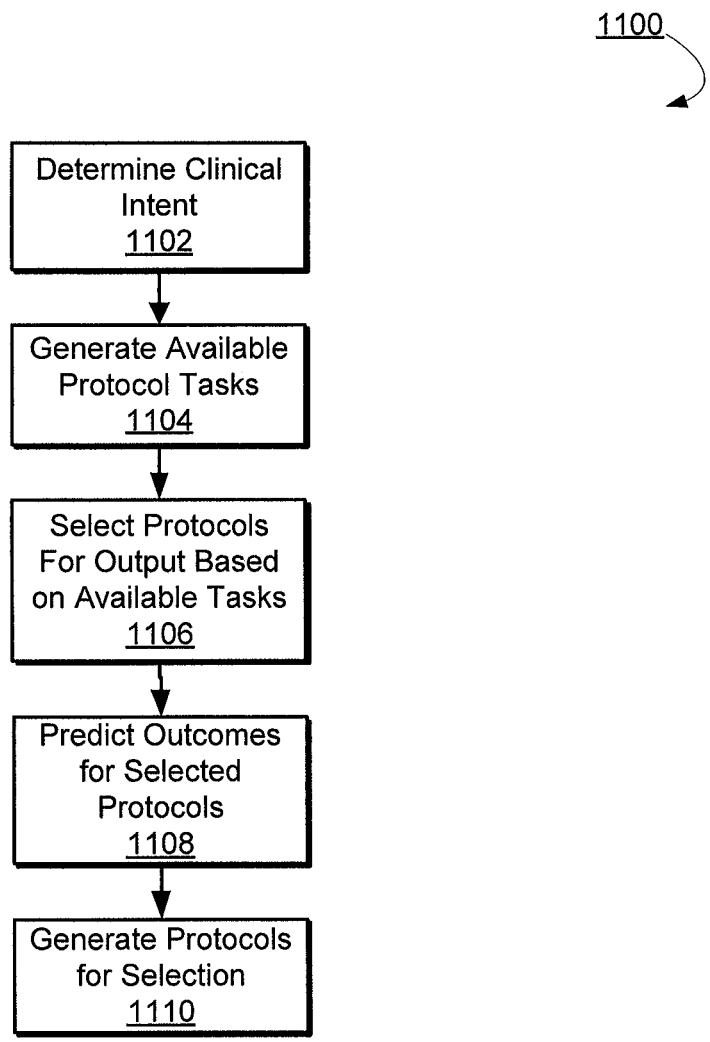
FIG. 11 is a flow diagram illustrating an exemplary method for selecting a second plurality of clinical protocols, in accordance with some embodiments of the present disclosure.

FIG. 11 depicts a flow diagram illustrating an exemplary method 1100 for selecting a second plurality of clinical protocols (e.g., as described in Step 522), in accordance with some embodiments of the present disclosure.

At Step 1102, adaptive treatment engine 212 may determine clinical intent. According to some embodiments, integration engine 412 may consider diagnosis information learned from import and analysis of the intermediate data (e.g., Step 522), access medical device configuration 724 from protocol database 700, and/or execute one or more tasks from task database 432 to determine clinical intent (e.g., perform cancer radiation therapy to achieve a certain measurable goal, to apply radiation in certain (perhaps limited) quantities, to reduce the size of a tumor by a measurable amount, to effect a change that can be measured by a clinical test, etc.).

At Step 1104, integration engine 412 may select available protocol tasks from task database 800 based on the diagnosis and/or analysis of the medical image. For example, integration engine 412 may determine a diagnosis M, and access static task rules 820 to determine from task-protocol map 822 that a particular set of tasks, say 11, 12, and 14, are appropriate for diagnosis M. Integration engine 412 may nevertheless use available protocol tasks 15, 16, and 12 to determine one or more protocols. The determination made by integration engine 412 may be determined by information accessed in the protocol database 700.

At Step 1006, integration engine 412 may select candidate protocols for treatment based on the available tasks. The available tasks may be selected based on static task rules 820, which provide links in task-protocol map 822 between the protocol (e.g., protocol 702) and the various tasks that are clinically acceptable for that protocol. Integration engine 412 may further analyze the selected protocols by predicting the outcomes for each candidate protocol.

At Step 1108, integration engine 412 may predict protocol outcomes for the selected protocols. Integration engine 412 may predict the outcomes in real time, based on available information including medical device configuration 724 persistent case data 604, patient data 606, adaptive case data 608, reference protocol data 710 and/or adaptive protocol data 708. Predictions may be based, for example, on efficacy data 624 in association (e.g., correlated with) protocol proposal data 622, protocol deviation efficacy record 712 and other records indicating similar information as assimilated from protocol proposal history and task execution data 720.

At Step 1110, integration engine 412 may generate protocols for selection. The generated protocols may be based on the relative predictions made at Step 1108, in view of a formalized treatment objective 632 and/or a clinical objective deviation 630.

FIG. 12 is a flow diagram illustrating an adaptive radiotherapy treatment, in accordance with some embodiments of the present disclosure and may be implemented using system 400.

At Step 1210, medical device controller 414 may import medical image data indicative of a biological structure observed in patient 426. The medial image data may be provided by a medical device (e.g., medical devices 416 and 418). For example, medical imaging device 416 may receive a signal from adaptive treatment engine 212 to provide a medical image (e.g., a CAT scan). Medical imaging device 416 may perform the scan of patient 426, save the scan data (the medical image data) to a local memory, and transmit the data via device bus 422 to adaptive treatment engine 212.

At Step 1212, integration engine 412 may perform and/or initiate performance of image processing to analyze the image data to determine the topography of structures in the data.

At Step 1214, after referencing case database 600, protocol database 700, and task database 800, integration engine 412 may select a first plurality of therapeutic protocols for delineation of the structure.

At Step 1216, adaptive treatment engine 212 may select the first plurality of therapeutic protocols and present the candidate protocols to the medical professional.

At Step 1218, adaptive treatment engine 212 may make the treatment decision either independently or with the approval of a qualified medical professional.

At Step 1220 the treatment is approved and delivered.

At Step 1222, treatment data is received based on the delivered treatment. For example, efficacy data relating to the delivered treatment can be received. Efficacy data can include information about tumor shrinkage, delivered radiation to OARs, and the like.

At Step 1224, therapeutic agent module 210 may analyze the intermediate results, and determine that an adaptive second treatment is necessary.

At Step 1226, adaptive treatment engine 212 may select, based on the reference protocol data and adaptive protocol data, may select a second treatment plan for determining organs at risk (OAR) and targeting using a second plurality of therapeutic protocols.

At Step 1228, the selected second treatment plan is approved.

At Step 1230, a treatment decision is again made.

At Step 1232 the second treatment plan is delivered. Therapeutic agent module 210 may be configured to manage a variety of adaptive radiotherapy treatments, including, for example, dose prescription and approval, and dose delivery and recording, among others.

FIG. 13 depicts an exemplary adaptive treatment management treatment plan 1300, according to some embodiments. After selecting the first plurality of candidate protocols 1216, for example, to initiate delineation tasks for determining organs at risk (OAR) and targeting, adaptive treatment engine 212 may present the options via an output device (e.g., output devices 305 and/or medical device interface 420). Various protocols (e.g., clinical objectives, goals, and/or treatment options) 1302, 1304, 1306 and 1308 are depicted, each with their respective fraction plans (e.g., 1310) shown in line with their respective tasks 1318. Adaptive treatment engine 210 may present each of the protocols (e.g., treatment options) 1302, 1304, 1306, and 1308 in a way so as to provide a relative comparison of all four options. Although not shown, protocols 1304, 1306, and 1308 may include a protocol structure similar to protocol 1302, but with different tasks presented in a format comparable to protocol 1302.

FIG. 14 illustrates an adaptive radiotherapy treatment management protocol 1302, in accordance with some embodiments of the present disclosure. At Step 1402, protocol 1302 may include a task for acquiring data. After data is acquired, protocol 1302 may perform three tasks 1404, 1406 and 1408 in parallel. For example, at 1404, protocol 1302 may include using an imaging device to obtain one or more images showing a contour the target tumor. At 1406, protocol 1302 may include a task to contour the organs at risk. At 1408, protocol 1302 may further apply an applicator and/or catheter to the patient 426. Although tasks 1404 and 1406 require approval, some tasks (e.g., Task 1408) may be run without approval. At 1410, tasks 1404 and 1406 are approved or rejected. At 1412, protocol 1302 may include a task for inverse dose planning, including contours. At 1414 the inverse dose planning is approved and protocol 1302 may end.

According to some embodiments, protocol 1302 may be modified from its standard protocol description (e.g., standard protocol description 732) to include new Tasks 1416 and 1418. Accordingly, the protocol may deviate from the standard description. Protocol 1302 may record the deviations to protocol deviation record 714. After delivery of the deviated protocol, adaptive treatment engine 212 may determine an efficacy of the protocol, and record the efficacy in protocol deviation efficacy record 712. Although protocol 1302, as depicted in FIG. 14, includes a particular number of steps, it should be appreciated that protocol 1302 is exemplary only. Therapeutic agent module 210 may include any number of clinically acceptable treatment protocols that may include any number of treatment tasks, in any number of particular orders.

The present disclosure describes an adaptive treatment management system with independent treatment modeling and a workflow management engine. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed, and the combined functionality of the set of modules available to the user covers the requirements of the application domain. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of the disclosed embodiments being indicated by the following claims.

What is claimed is:

1. A system for generating treatment plans, the system comprising:
 a clinical database for storing therapeutic protocols, wherein each therapeutic protocol reflects a plurality of treatment tasks; and
 a treatment engine operatively connected to the clinical database, the treatment engine including:
 a medical device controller configured to obtain diagnostic information for a patient; and
 at least one processor programmed to:
 select a first plurality of therapeutic protocols from the clinical database, wherein the selection is based on the obtained diagnostic information;
 calculate a treatment efficacy probability for each protocol in the first plurality of therapeutic protocols based on a clinical objective, the treatment efficacy probability representing a probability that a particular protocol will be effective at reaching a particular clinical objective for particular diagnostic information;
 develop a first treatment plan from the first plurality of therapeutic protocols based on the clinical objective and the treatment efficacy probabilities;
 generate a first record associated with the patient that identifies the diagnostic information and the first treatment plan developed from the first plurality of therapeutic protocols;
 evaluate, during a course of execution of the first treatment plan, a task token input comprising intermediate data indicating an altered patient state due to the course of execution of the first treatment plan;
 determine, based on the task token input comprising the intermediate data, treatment efficacy representing effectiveness of the first treatment plan in reaching the clinical objective due to the course of execution of the first treatment plan;
 generate a case token output comprising the determined treatment efficacy;
 select a second treatment plan using a second plurality of therapeutic protocols based on the case token output including the determined treatment efficacy and new diagnostic information; and
 copy and modify the first record based on the case token output indicating that the treatment efficacy has been updated to create a second record and to link the first record with the second record that identifies the new diagnostic information and the second treatment plan.

2. The system of claim 1, wherein the task token input represents an exchange of information that correlates case specific information with information from outside of case space, and wherein the at least one processor is further programmed to:
 update a case record, wherein the update includes the first plurality of therapeutic protocols, the second plurality of protocols, the intermediate data, and the second treatment plan.

3. The system of claim 2, wherein the case space includes a body of clinical data and represents evolution of a managed case, wherein the information from outside of the case space includes an acquired image of the patient or one or more treatment machine parameters, and wherein the at least one processor is further programmed to:
 determine an efficacy of the second treatment plan; and
 generate a protocol efficacy record.

4. The system of claim 1, wherein the at least one processor is further programmed to:
 determine a clinical objective for an adaptive cancer treatment;
 analyze a medical image to obtain a clinically relevant data point; and
 parse the linked first and second records to identify a correlation, based on the clinically relevant data point, between the first and second treatment plans used in executing the first and second treatment plans for the patient.

5. The system of claim 1, wherein evaluating the intermediate data comprises:
 determining a clinical intent; and
 evaluating the intermediate data with respect to the clinical intent.

6. The system of claim 1, wherein the diagnostic information comprises one or more medical images, and wherein the at least one processor is further programmed to:
 obtain a set of records that include the first treatment plan used in previous treatment sessions for other patients along with respective efficacy information;
 identify a group of the records that indicate positive tumor response given circumstances determined from the one or more medical images; and
 determine a correlation between the group of records and the circumstances determined from the one or more medical images.

7. The system of claim 1, wherein generating the first plurality of therapeutic protocols comprises:
 determining a clinical intent;
 generating a plurality of available protocol tasks;
 selecting at least two protocols from a protocol database based on the available protocol tasks;
 predicting an outcome for each of the at least two selected protocols; and
 generating the first plurality of therapeutic protocols based on the predicted outcomes.

8. The system of claim 7, wherein the plurality of available protocol tasks is indicative of a permissible protocol action.

9. The system of claim 7, wherein the plurality of available protocol tasks is generated based on the diagnostic information and the clinical intent.

10. The system of claim 9, wherein evaluating the intermediate data further comprises:
 selectively generating a new clinical intent based on the intermediate data.

11. The system of claim 10, wherein generating the second plurality of protocols comprises:
 generating a second plurality of available protocol tasks indicative of a permissible protocol action;

selecting at least two protocols from a protocol database;
predicting treatment efficacy probabilities for each of the at least two selected protocols; and
generating the second plurality of protocols based on the treatment efficacy probabilities.

12. The system of claim 11, wherein the at least two protocols from a protocol database are selected based on the intermediate data and one of the clinical intent and the new clinical intent.

13. A computer-implemented method for generating treatment plans, the method comprising:
selecting, using at least one processor, a first plurality of therapeutic protocols from a clinical database based on diagnostic information associated with a patient;
determining, using the least one processor, a clinical objective for a given treatment plan;
calculating, using the least one processor, a treatment efficacy probability for each protocol in the first plurality of therapeutic protocols based on the clinical objective, the treatment efficacy probability representing a probability that a particular protocol will be effective at reaching a particular clinical objective for particular diagnostic information;
developing, using the least one processor, a first treatment plan from the first plurality of therapeutic protocols based on the clinical objective and the treatment efficacy probabilities;
generating a first record associated with the patient that identifies the diagnostic information and the first treatment plan developed from the first plurality of therapeutic protocols;
evaluating, using the least one processor, during a course of execution of the first treatment plan, a task token input comprising intermediate data indicating an altered patient state due to the course of execution of the first treatment plan;
determining, based on the task token input comprising the intermediate data, treatment efficacy representing effectiveness of the first treatment plan in reaching the clinical objective due to the course of execution of the first treatment plan;
generating a case token output comprising the determined treatment efficacy;
selecting, using the least one processor, a second treatment plan using a second plurality of therapeutic protocols based on the case token output including the determined treatment efficacy and new diagnostic information; and
copying and modifying the first record based on the case token output indicating that the treatment efficacy has been updated to create a second record and to link the first record with the second record that identifies the new diagnostic information and the second treatment plan.

14. The computer-implemented method of claim 13, further comprising:
updating a case record, wherein the updating includes the first plurality of therapeutic protocols, the second plurality of protocols, the intermediate data, and the second treatment plan.

15. The computer-implemented method of claim 13, further comprising:
determining an efficacy of the second treatment plan; and
generating a protocol efficacy record.

16. The computer-implemented method of claim 13, wherein evaluating the intermediate data comprises:
evaluating the intermediate data with respect to the clinical objective.

17. The computer-implemented method of claim 13, wherein generating the first plurality of therapeutic protocols comprises:
generating a plurality of available protocol tasks;
selecting at least two protocols from a protocol database based on the available protocol tasks;
predicting an outcome for each of the at least two selected protocols; and
generating the first plurality of therapeutic protocols based on the predicted outcomes.

18. The computer-implemented method of claim 17 wherein the plurality of available protocol tasks is indicative of a permissible protocol action.

19. The computer-implemented method of claim 17, wherein the plurality of available protocol tasks is generated based on the diagnostic information and the clinical objective.

20. The computer-implemented method of claim 19, wherein evaluating the intermediate data further comprises:
selectively generating a new clinical objective based on the intermediate data.

21. The computer-implemented method of claim 19, wherein generating the second plurality of protocols comprises:
generating a second plurality of available protocol tasks indicative of a permissible protocol action;
selecting at least two protocols from a protocol database;
predicting the outcome for each of the at least two selected protocols; and
generating the second plurality of protocols based on the predicted outcomes.

22. The computer-implemented method of claim 21, wherein the at least two protocols from a protocol database are selected based on the intermediate data and one of the clinical objective and the new clinical objective.

23. A non-transitory computer readable storage medium that stores instructions that are executable by at least one processor to perform a method for adaptive cancer treatment, the method comprising:
selecting a first plurality of therapeutic protocols from a clinical database based on diagnostic information associated with a patient;
determining a clinical objective for the treatment;
calculating a treatment efficacy probability for each protocol in the first plurality of therapeutic protocols based on the clinical objective, the treatment efficacy probability representing a probability that a particular protocol will be effective at reaching a particular clinical objective for particular diagnostic information;
developing a first treatment plan from the first plurality of therapeutic protocols based on the clinical objective and the treatment efficacy probabilities;
generating a first record associated with the patient that identifies the diagnostic information and the first treatment plan developed from the first plurality of therapeutic protocols;
evaluating, during a course of execution of the first treatment plan, a task token input comprising intermediate data indicating an altered patient state due to the course of execution of the first treatment plan;
determining, based on the task token input comprising the intermediate data, treatment efficacy representing effectiveness of the first treatment plan in reaching the clinical objective due to the course of execution of the first treatment plan;

generating a case token output comprising the determined treatment efficacy;

selecting a second treatment plan using a second plurality of therapeutic protocols based on the case token output including the determined treatment efficacy and new diagnostic information; and copying and modifying the first record based on the case token output indicating that the treatment efficacy has been updated to create a second record and to link the first record with the second record that identifies the new diagnostic information and the second treatment plan.

\* \* \* \* \*